(12) United States Patent
Vranes et al.

(10) Patent No.: US 11,078,527 B2
(45) Date of Patent: Aug. 3, 2021

(54) METHOD FOR QUANTIFYING AND/OR DETECTING HUMAN MALE DNA

(71) Applicant: QIAGEN GmbH, Hilden (DE)

(72) Inventors: Miroslav Vranes, Hilden (DE); Ralf Peist, Hilden (DE); Mario Scherer, Hilden (DE); Stefan Otto Cornelius, Hilden (DE); Margaretha König, Hilden (DE)

(73) Assignee: Qiagen GmbH, Hilden (DE)

( * ) Notice: Subject to any disclaimer, the term of this patent is extended or adjusted under 35 U.S.C. 154(b) by 313 days.

(21) Appl. No.: 16/333,076

(22) PCT Filed: Sep. 15, 2017

(86) PCT No.: PCT/EP2017/073311
§ 371 (c)(1),
(2) Date: Mar. 13, 2019

(87) PCT Pub. No.: WO2018/054783
PCT Pub. Date: Mar. 29, 2018

(65) Prior Publication Data
US 2019/0249233 A1  Aug. 15, 2019

(30) Foreign Application Priority Data
Sep. 22, 2016 (EP) .................................. 16189210

(51) Int. Cl.
*C12Q 1/68* (2018.01)
*C12Q 1/6827* (2018.01)
(Continued)

(52) U.S. Cl.
CPC ........... *C12Q 1/6827* (2013.01); *C12Q 1/686* (2013.01); *C12Q 1/6806* (2013.01);
(Continued)

(58) Field of Classification Search
CPC ....................................................... C12Q 1/68
(Continued)

(56) References Cited

U.S. PATENT DOCUMENTS 7,374,927 B2 *   5/2008  Palma ................. C12Q 1/6883
                                                   435/287.2
2003/0203870 A1  10/2003  Blatt et al.
(Continued)

FOREIGN PATENT DOCUMENTS

WO         0159103 A2    8/2001
WO      2012113577 A1    8/2012
(Continued)

OTHER PUBLICATIONS

International Search Report dated Oct. 23, 2017 filed in PCT/EP2017/073311.

*Primary Examiner* — Aaron A Priest
(74) *Attorney, Agent, or Firm* — Rankin, Hill & Clark LLP

(57) ABSTRACT

According to a first aspect of the present invention, a method is provided for detecting and/or quantifying male genomic DNA in a sample, wherein the method comprises the step of amplification of a multicopy locus within the human Y-chromosome (MCL-Y), wherein said locus shares at least 80% sequence identity to a sequence according to SEQ ID NO. 3 over a stretch of at least 60 base pairs (bp). A second aspect of the present invention relates to a primer or primer pair which hybridizes under stringent conditions to a sequence according to SEQ ID NO. 3 and/or any of 4 to 11. The invention also relates to a kit.

8 Claims, 4 Drawing Sheets
Specification includes a Sequence Listing.

SEQ ID NO. 2        SEQ ID NO. 1

Probe SEQ ID NO. 12

Probe SEQ ID NO. 16

← SEQ ID NO. 15
← SEQ ID NO. 13
← SEQ ID NO. 14

(51) Int. Cl.
*C12Q 1/6879* (2018.01)
*C12Q 1/6851* (2018.01)
*C12Q 1/6806* (2018.01)
*C12Q 1/686* (2018.01)
*C12Q 1/6876* (2018.01)

(52) U.S. Cl.
CPC ......... *C12Q 1/6851* (2013.01); *C12Q 1/6876* (2013.01); *C12Q 1/6879* (2013.01); *C12Q 2525/151* (2013.01); *C12Q 2600/16* (2013.01); *C12Q 2600/166* (2013.01)

(58) Field of Classification Search
USPC ....................................................... 435/6.12
See application file for complete search history.

(56) References Cited

U.S. PATENT DOCUMENTS

| | | |
|---|---|---|
| 2005/0272080 A1 | 12/2005 | Palma et al. |
| 2014/0147843 A1 | 5/2014 | Di Pasquale et al. |

FOREIGN PATENT DOCUMENTS

| | | | | |
|---|---|---|---|---|
| WO | WO-2012113577 A1 * | 8/2012 | ........... | C12Q 1/6879 |
| WO | 2015013455 A2 | 1/2015 | | |
| WO | WO-2015013455 A2 * | 1/2015 | ........... | C12Q 1/6886 |

\* cited by examiner

|  | Invention |
|---|---|
| undegraded male DNA | 1,0 |
| 1500bp male DNA | 1,7 |
| 500bp male DNA | 3,3 |
| 300bp male DNA | 6,4 |
| 150bp male DNA | 188,1 |

SEQUENCE LISTING

<160> NUMBER OF SEQ ID NOS: 45

<210> SEQ ID NO 1
<211> LENGTH: 22
<212> TYPE: DNA
<213> ORGANISM: Artificial Sequence
<220> FEATURE:
<223> OTHER INFORMATION: Synthetic Primer

```
<400> SEQUENCE: 1
gaaaggcctc atcagggctc ag                                            22

<210> SEQ ID NO 2
<211> LENGTH: 27
<212> TYPE: DNA
<213> ORGANISM: Artificial Sequence
<220> FEATURE:
<223> OTHER INFORMATION: Synthetic Primer

<400> SEQUENCE: 2
tcctcactgg gaaacatgag gaatgac                                       27

<210> SEQ ID NO 3
<211> LENGTH: 81
<212> TYPE: DNA
<213> ORGANISM: Homo sapiens

<400> SEQUENCE: 3
gaaaggcctc atcagggctc agaaaggtga cccaagcagc tgggaacaca cggggtcatt   60
cctcatgttt cccagtgagg a                                             81

<210> SEQ ID NO 4
<211> LENGTH: 81
<212> TYPE: DNA
<213> ORGANISM: Homo sapiens

<400> SEQUENCE: 4
gaaaggcctc atcagggctc agaaaggtga cccaagcagc tgggaacaca cggggtcatt   60
cctcatgttt cccagtgagg a                                             81

<210> SEQ ID NO 5
<211> LENGTH: 81
<212> TYPE: DNA
<213> ORGANISM: Homo sapiens

<400> SEQUENCE: 5
gaaaggcctc atcagggctc agaaaggtga cccaagcagc tgggaacaca tggggtcatt   60
cctcatgttt cccagtgagg a                                             81

<210> SEQ ID NO 6
<211> LENGTH: 81
<212> TYPE: DNA
<213> ORGANISM: Homo sapiens

<400> SEQUENCE: 6
gaaaggcctc atcagggctc agaaaggtga cccaagcagc tgggaacaca cggggtcatt   60
cctcatgttt cccagtgagg a                                             81

<210> SEQ ID NO 7
<211> LENGTH: 81
<212> TYPE: DNA
<213> ORGANISM: Homo sapiens

<400> SEQUENCE: 7
gaaaggcctc atcagggctc agaaaggtga cccaagcagc tgggaacaca cggggtcatt   60
cctcatgttt cccagtgagg a                                             81

<210> SEQ ID NO 8
<211> LENGTH: 81
```

-continued

<210> SEQ ID NO 8
<211> LENGTH: 81
<212> TYPE: DNA
<213> ORGANISM: Homo sapiens

<400> SEQUENCE: 8
gaaaggcctc atcagggctc agaaaggtga cccaagcagc tgggaacaca cggggtcatt    60
cctcatgttt cccagtgagg a                                              81

<210> SEQ ID NO 9
<211> LENGTH: 81
<212> TYPE: DNA
<213> ORGANISM: Homo sapiens

<400> SEQUENCE: 9
gaaaggcctc atcagggctc agaaaggtga cccaagcagc tgggaacaca cggggtcatt    60
cctcatgttt cccagtgagg a                                              81

<210> SEQ ID NO 10
<211> LENGTH: 81
<212> TYPE: DNA
<213> ORGANISM: Homo sapiens

<400> SEQUENCE: 10
gaaaggcctc atcagggctc agaaaggtga cccaagcagc tgggaacaca tggggtcatt    60
cctcatgttt cccagtgagg a                                              81

<210> SEQ ID NO 11
<211> LENGTH: 81
<212> TYPE: DNA
<213> ORGANISM: Homo sapiens

<400> SEQUENCE: 11
gaaaggcctc atcagggctc agaaaggtga cccaagcagc tgggaacaca cggggtcatt    60
cctcatgttt cccagtgagg a                                              81

<210> SEQ ID NO 12
<211> LENGTH: 25
<212> TYPE: DNA
<213> ORGANISM: Artificial Sequence
<220> FEATURE:
<223> OTHER INFORMATION: Synthetic Probe

<400> SEQUENCE: 12
ggtgacccaa gcagctggga acaca                                          25

<210> SEQ ID NO 13
<211> LENGTH: 26
<212> TYPE: DNA
<213> ORGANISM: Artificial Sequence
<220> FEATURE:
<223> OTHER INFORMATION: Synthetic Primer

<400> SEQUENCE: 13
catgaacgtc ctggattctg tcactc                                         26

<210> SEQ ID NO 14
<211> LENGTH: 33
<212> TYPE: DNA
<213> ORGANISM: Artificial Sequence
<220> FEATURE:
<223> OTHER INFORMATION: Synthetic Primer

<400> SEQUENCE: 14
tcactctctg tcttcctctc aaggaatttc tac                          33

<210> SEQ ID NO 15
<211> LENGTH: 26
<212> TYPE: DNA
<213> ORGANISM: Artificial Sequence
<220> FEATURE:
<223> OTHER INFORMATION: Synthetic Primer

<400> SEQUENCE: 15
gccatgaacg tcctggattc tgtcac                                 26

<210> SEQ ID NO 16
<211> LENGTH: 25
<212> TYPE: DNA
<213> ORGANISM: Artificial Sequence
<220> FEATURE:
<223> OTHER INFORMATION: Synthetic Probe

<400> SEQUENCE: 16
caggctccct gaataggcag gtgtg                                  25

<210> SEQ ID NO 17
<211> LENGTH: 359
<212> TYPE: DNA
<213> ORGANISM: Homo sapiens

<400> SEQUENCE: 17
tcctcactgg gaaacatgag gaatgacccc gtgtgttccc agctgcttgg gtcacctttc     60
tgagccctga tgaggccttt cccgattgag tcccctgaca gatcctatgt aaggacctgt    120
ggcgcaatcc cctgcaatac tacaagagga tgaagccacc tgaagaggga acagagacgt    180
caggtgagcc gttagttggc actggagctg tttgatgccc agtataaggg ggttgacaca    240
cctgcctatt cagggagcct gggtgctcat ttcagaaatg tagaaattga ggctcctttc    300
gtacatgtag aaattccttg agaggaagac agagagtgac agaatccagg acgttcatg    359

<210> SEQ ID NO 18
<211> LENGTH: 359
<212> TYPE: DNA
<213> ORGANISM: Homo sapiens

<400> SEQUENCE: 18
tcctcactgg gaaacatgag gaatgacccc gtgtgttccc agctgcttgg gtcacctttc     60
tgagccctga tgaggccttt cccgattgag tcccctgaca gatcctatgt aaggacctgt    120
ggcgcaatcc cctgcaatac tacaagagga tgaagccacc tgaagaggga acagagacgt    180
caggtgagcc gttagttggc actggagctg tttgatgccc agtataaggg ggttgacaca    240
cctgcctatt cagggagcct gggtgctcat ttcagaaatg tagaaattga ggctcctttc    300
gtacatgtag aaattccttg agaggaagac agagagtgac agaatccagg acgttcatg    359

<210> SEQ ID NO 19
<211> LENGTH: 359
<212> TYPE: DNA
<213> ORGANISM: Homo sapiens

<400> SEQUENCE: 19
tcctcactgg gaaacatgag gaatgacccc atgtgttccc agctgcttgg gtcacctttc     60
tgagccctga tgaggccttt cccgattgag tcccctgaca gatcctatgt aaggacctgt    120
ggcgcaatcc cctgcaatac tacaagagga tgaagccacc tgaagaggga acagagacgt    180

```
caggtgagcc gttagttggc actggagctg tttgatgccc agtataaggg ggttgacaca    240
cctgcctatt cagggagcct gggtgctcat ttcagaaatg tagaaattga ggctcctttc    300
gtacatgtag aaattccttg agaggaagac agagagtgac agaatccagg acgttcatg    359

<210> SEQ ID NO 20
<211> LENGTH: 357
<212> TYPE: DNA
<213> ORGANISM: Homo sapiens

<400> SEQUENCE: 20
tcctcactgg gaaacatgag gaatgacccc gtgtgttccc agctgcttgg gtcacctttc     60
tgagccctga tgaggccttt cccgattgag tcccctgaca gatcctatgt aaggacctgt    120
ggcgcaatcc cctgcaatac tacaaggaga tgaagccacc tgaagaggga acagagacgt    180
caggtgagcc gttagttggc actggagctg tttgatgcgc agtataaggg ggttgacaca    240
cctgcctatt cagggagcct gggtgctcat ttcagaaatg tagaaactga ggctcctttc    300
gtacatgtag aaattccttg agaggaagac agagtgacag aatccaggac gttcatg      357

<210> SEQ ID NO 21
<211> LENGTH: 359
<212> TYPE: DNA
<213> ORGANISM: Homo sapiens

<400> SEQUENCE: 21
tcctcactgg gaaacatgag gaatgacccc gtgtgttccc agctgcttgg gtcacctttc     60
tgagccctga tgaggccttt cccgattgag tcccctgaca gatcctatgt aaggacctgt    120
ggcgcaatcc cctgcaatac tacaaggaga tgaagccacc tgaagaggga acagagacgt    180
caggtgagcc gttagttggc actggagctg tttgatgccc agtataaggg ggttgacaca    240
cctgcctatt cagggagcct gggtgctcat ttcagaaatg tagaaattga ggctcctttc    300
gtacatgtag aaattccttg agaggaagac agagagtgac agaatccagg acgttcatg    359

<210> SEQ ID NO 22
<211> LENGTH: 359
<212> TYPE: DNA
<213> ORGANISM: Homo sapiens

<400> SEQUENCE: 22
tcctcactgg gaaacatgag gaatgacccc gtgtgttccc agctgcttgg gtcacctttc     60
tgagccctga tgaggccttt cccgattgag tcccctgaca gatcctatgt aaggacctgt    120
ggcgcaatcc cctgcaatac tacaaggaga tgaagccacc tgaagaggga acagagacgt    180
caggtgagcc gttagttggc actggagctg tttgatgccc agtataaggg ggttgacaca    240
cctgcctatt cagggagcct gggtgctcat ttcagaaatg tagaaattga ggctcctttc    300
gtacatgtag aaattccttg agaggaagac agagagtgac agaatccagg acgttcatg    359

<210> SEQ ID NO 23
<211> LENGTH: 359
<212> TYPE: DNA
<213> ORGANISM: Homo sapiens

<400> SEQUENCE: 23
tcctcactgg gaaacatgag gaatgacccc gtgtgttccc agctgcttgg gtcacctttc     60
tgagccctga tgaggccttt cccgattgag tcccctgaca gatcctatgt aaggacctgt    120
```

| | |
|---|---|
| ggcgcaatcc cctgcaatac tacaagagga tgaagccacc tgaagaggga acagagacgt | 180 |
| caggtgagcc gttagttggc actggagctg tttgatgccc agtataaggg ggttgacaca | 240 |
| cctgccatt cagggagcct gggtgctcat ttcagaaatg tagaaattga ggctcctttc | 300 |
| gtacatgtag aaattccttg agaggaagac agagagtgac agaatccagg acgttcatg | 359 |

<210> SEQ ID NO 24
<211> LENGTH: 359
<212> TYPE: DNA
<213> ORGANISM: Homo sapiens

<400> SEQUENCE: 24

| | |
|---|---|
| tcctcactgg gaaacatgag gaatgacccc atgtgttccc agctgcttgg gtcacctttc | 60 |
| tgagccctga tgaggccttt cccgattgag tccctgaca gatcctatgt aaggacctgt | 120 |
| ggcgcaatcc cctgcaatac tacaagagga tgaagccacc tgaagaggga acagagacgt | 180 |
| caggtgagcc gttagttggc actggagctg tttgatgccc agtataaggg ggttgacaca | 240 |
| cctgccatt cagggagcct gggtgctcat ttcagaaatg tagaaattga ggctcctttc | 300 |
| gtacatgtag aaattccttg agaggaagac agagagtgac agaatccagg acgttcatg | 359 |

<210> SEQ ID NO 25
<211> LENGTH: 359
<212> TYPE: DNA
<213> ORGANISM: Homo sapiens

<400> SEQUENCE: 25

| | |
|---|---|
| tcctcactgg gaaacatgag gaatgacccc gtgtgttccc agctgcttgg gtcacctttc | 60 |
| tgagccctga tgaggccttt cccgattgag tccctgaca gatcctatgt aaggacctgt | 120 |
| ggcgcaatcc cctgcaatac tacaagagga tgaagccacc tgaagaggga acagagacgt | 180 |
| caggtgagcc gttagttggc actggagctg tttgatgccc agtataaggg ggttgacaca | 240 |
| cctgccatt cagggagcct gggtgctcat ttcagaaatg tagaaattga ggctcctttc | 300 |
| gtacatgtag aaattccttg agaggaagac agagagtgac agaatccagg acgttcatg | 359 |

<210> SEQ ID NO 26
<211> LENGTH: 340
<212> TYPE: DNA
<213> ORGANISM: Homo sapiens

<400> SEQUENCE: 26

| | |
|---|---|
| tcctcactgg gaaacatgag gaatgacccc atgtgttccc agctgcttgg gtcaccattc | 60 |
| tgagtcctga tgaggccttt cccgatggat tccctgaca gatcctatgt aaggacctgt | 120 |
| ggtgcaatcc cctgcaatcc tacaagagga tgaagccacc tgaagaggga acagagattt | 180 |
| caggtgagct gttcagttgg aactgaagct ttttgatccc caggataagg aggttgacac | 240 |
| acctgcctat tcaggagcc tggaggctca tttcagaaat gtagaaattg agcctccttt | 300 |
| catacatgta gaaattcctt gagaggaaga cagagtgtga | 340 |

<210> SEQ ID NO 27
<211> LENGTH: 339
<212> TYPE: DNA
<213> ORGANISM: Homo sapiens

<400> SEQUENCE: 27

| | |
|---|---|
| tcctcactgg gaaacatgag gaatgacccc gtgtgttccc agctgcttgg gtcacctttc | 60 |
| tgagccctga tgaggccttt cccgattgag tccctgaca gatcctatgt aaggacctgt | 120 |

```
ggcgcaatcc cctgcaatac tacaagagga tgaagccacc tgaagaggga acagagacgt    180
caggtgagcc gttagttggc actggagctg tttgatgccc agtataaggg ggttgacaca    240
cctgcctatt cagggagcct gggtgctcat ttcagaaatg tagaaattga ggctcctttc    300
gtacatgtag aaattccttg agaggaagac agagagtga                          339
```

<210> SEQ ID NO 28
<211> LENGTH: 339
<212> TYPE: DNA
<213> ORGANISM: Homo sapiens

<400> SEQUENCE: 28

```
tcctcactgg gaaacatgag gaatgacccc gtgtgttccc agctgcttgg gtcacctttc     60
tgagccctga tgaggccttt cccgattgag tccctgaca gatcctatgt aaggacctgt    120
ggcgcaatcc cctgcaatac tacaagagga tgaagccacc tgaagaggga acagagacgt    180
caggtgagcc gttagttggc actggagctg tttgatgccc agtataaggg ggttgacaca    240
cctgcctatt cagggagcct gggtgctcat ttcagaaatg tagaaattga ggctcctttc    300
gtacatgtag aaattccttg agaggaagac agagagtga                          339
```

<210> SEQ ID NO 29
<211> LENGTH: 339
<212> TYPE: DNA
<213> ORGANISM: Homo sapiens

<400> SEQUENCE: 29

```
tcctcactgg gaaacatgag gaatgacccc atgtgttccc agctgcttgg gtcacctttc     60
tgagccctga tgaggccttt cccgattgag tccctgaca gatcctatgt aaggacctgt    120
ggcgcaatcc cctgcaatac tacaagagga tgaagccacc tgaagaggga acagagacgt    180
caggtgagcc gttagttggc actggagctg tttgatgccc agtataaggg ggttgacaca    240
cctgcctatt cagggagcct gggtgctcat ttcagaaatg tagaaattga ggctcctttc    300
gtacatgtag aaattccttg agaggaagac agagagtga                          339
```

<210> SEQ ID NO 30
<211> LENGTH: 339
<212> TYPE: DNA
<213> ORGANISM: Homo sapiens

<400> SEQUENCE: 30

```
tcctcactgg gaaacatgag gaatgacccc gtgtgttccc agctgcttgg gtcacctttc     60
tgagccctga tgaggccttt cccgattgag tccctgaca gatcctatgt aaggacctgt    120
ggcgcaatcc cctgcaatac tacaagagga tgaagccacc tgaagaggga acagagacgt    180
caggtgagcc gttagttggc actggagctg tttgatgcgc agtataaggg ggttgacaca    240
cctgcctatt cagggagcct gggtgctcat ttcagaaatg tagaaactga ggctcctttc    300
gtacatgtag aaattccttg agaggaagac agagtgaca                          339
```

<210> SEQ ID NO 31
<211> LENGTH: 339
<212> TYPE: DNA
<213> ORGANISM: Homo sapiens

<400> SEQUENCE: 31

```
tcctcactgg gaaacatgag gaatgacccc gtgtgttccc agctgcttgg gtcacctttc     60
```
tgagccctga tgaggccttt cccgattgag tccctgaca gatcctatgt aaggacctgt    120
ggcgcaatcc cctgcaatac tacaagagga tgaagccacc tgaagaggga acagagacgt    180
caggtgagcc gttagttggc actggagctg tttgatgccc agtataaggg ggttgacaca    240
cctgcctatt cagggagcct gggtgctcat ttcagaaatg tagaaattga ggctcctttc    300
gtacatgtag aaattccttg agaggaagac agagagtga                          339

<210> SEQ ID NO 32
<211> LENGTH: 339
<212> TYPE: DNA
<213> ORGANISM: Homo sapiens

<400> SEQUENCE: 32
tcctcactgg gaaacatgag gaatgacccc gtgtgttccc agctgcttgg gtcacctttc     60
tgagccctga tgaggccttt cccgattgag tccctgaca gatcctatgt aaggacctgt    120
ggcgcaatcc cctgcaatac tacaagagga tgaagccacc tgaagaggga acagagacgt    180
caggtgagcc gttagttggc actggagctg tttgatgccc agtataaggg ggttgacaca    240
cctgcctatt cagggagcct gggtgctcat ttcagaaatg tagaaattga ggctcctttc    300
gtacatgtag aaattccttg agaggaagac agagagtga                          339

<210> SEQ ID NO 33
<211> LENGTH: 339
<212> TYPE: DNA
<213> ORGANISM: Homo sapiens

<400> SEQUENCE: 33
tcctcactgg gaaacatgag gaatgacccc gtgtgttccc agctgcttgg gtcacctttc     60
tgagccctga tgaggccttt cccgattgag tccctgaca gatcctatgt aaggacctgt    120
ggcgcaatcc cctgcaatac tacaagagga tgaagccacc tgaagaggga acagagacgt    180
caggtgagcc gttagttggc actggagctg tttgatgccc agtataaggg ggttgacaca    240
cctgcctatt cagggagcct gggtgctcat ttcagaaatg tagaaattga ggctcctttc    300
gtacatgtag aaattccttg agaggaagac agagagtga                          339

<210> SEQ ID NO 34
<211> LENGTH: 339
<212> TYPE: DNA
<213> ORGANISM: Homo sapiens

<400> SEQUENCE: 34
tcctcactgg gaaacatgag gaatgacccc atgtgttccc agctgcttgg gtcacctttc     60
tgagccctga tgaggccttt cccgattgag tccctgaca gatcctatgt aaggacctgt    120
ggcgcaatcc cctgcaatac tacaagagga tgaagccacc tgaagaggga acagagacgt    180
caggtgagcc gttagttggc actggagctg tttgatgccc agtataaggg ggttgacaca    240
cctgcctatt cagggagcct gggtgctcat ttcagaaatg tagaaattga ggctcctttc    300
gtacatgtag aaattccttg agaggaagac agagagtga                          339

<210> SEQ ID NO 35
<211> LENGTH: 339
<212> TYPE: DNA
<213> ORGANISM: Homo sapiens

<400> SEQUENCE: 35
tcctcactgg gaaacatgag gaatgacccc gtgtgttccc agctgcttgg gtcacctttc     60

```
tgagccctga tgaggccttt cccgattgag tcccctgaca gatcctatgt aaggacctgt    120
ggcgcaatcc cctgcaatac tacaagagga tgaagccacc tgaagaggga acagagacgt    180
caggtgagcc gttagttggc actggagctg tttgatgccc agtataaggg ggttgacaca    240
cctgcctatt cagggagcct gggtgctcat ttcagaaatg tagaaattga ggctcctttc    300
gtacatgtag aaattccttg agaggaagac agagagtga                           339
```

<210> SEQ ID NO 36
<211> LENGTH: 362
<212> TYPE: DNA
<213> ORGANISM: Homo sapiens

<400> SEQUENCE: 36

```
tcctcactgg gaaacatgag gaatgacccc atgtgttccc agctgcttgg gtcaccattc     60
tgagtcctga tgaggccttt cccgatggat tcccctgaca gatcctatgt aaggacctgt    120
ggtgcaatcc cctgcaatcc tacaagagga tgaagccacc tgaagaggga acagagattt    180
caggtgagct gttcagttgg aactgaagct ttttgatccc caggataagg aggttgacac    240
acctgcctat tcagggagcc tggaggctca tttcagaaat gtagaaattg agcctccttt    300
catacatgta gaaattcctt gagaggaaga cagagtgtga cagaatccag gacattcatg    360
gc                                                                   362
```

<210> SEQ ID NO 37
<211> LENGTH: 361
<212> TYPE: DNA
<213> ORGANISM: Homo sapiens

<400> SEQUENCE: 37

```
tcctcactgg gaaacatgag gaatgacccc gtgtgttccc agctgcttgg gtcacctttc     60
tgagccctga tgaggccttt cccgattgag tcccctgaca gatcctatgt aaggacctgt    120
ggcgcaatcc cctgcaatac tacaagagga tgaagccacc tgaagaggga acagagacgt    180
caggtgagcc gttagttggc actggagctg tttgatgccc agtataaggg ggttgacaca    240
cctgcctatt cagggagcct gggtgctcat ttcagaaatg tagaaattga ggctcctttc    300
gtacatgtag aaattccttg agaggaagac agagagtgac agaatccagg acgttcatgg    360
c                                                                    361
```

<210> SEQ ID NO 38
<211> LENGTH: 361
<212> TYPE: DNA
<213> ORGANISM: Homo sapiens

<400> SEQUENCE: 38

```
tcctcactgg gaaacatgag gaatgacccc gtgtgttccc agctgcttgg gtcacctttc     60
tgagccctga tgaggccttt cccgattgag tcccctgaca gatcctatgt aaggacctgt    120
ggcgcaatcc cctgcaatac tacaagagga tgaagccacc tgaagaggga acagagacgt    180
caggtgagcc gttagttggc actggagctg tttgatgccc agtataaggg ggttgacaca    240
cctgcctatt cagggagcct gggtgctcat ttcagaaatg tagaaattga ggctcctttc    300
gtacatgtag aaattccttg agaggaagac agagagtgac agaatccagg acgttcatgg    360
c                                                                    361
```

<210> SEQ ID NO 39

-continued

```
<211> LENGTH: 361
<212> TYPE: DNA
<213> ORGANISM: Homo sapiens

<400> SEQUENCE: 39
tcctcactgg gaaacatgag gaatgacccc atgtgttccc agctgcttgg gtcacctttc    60
tgagccctga tgaggccttt cccgattgag tccoctgaca gatcctatgt aaggacctgt   120
ggcgcaatcc cctgcaatac tacaaggaga tgaagccacc tgaagaggga acagagacgt   180
caggtgagcc gttagttggc actggagctg tttgatgccc agtataaggg ggttgacaca   240
cctgcctatt cagggagcct gggtgctcat ttcagaaatg tagaaattga ggctcctttc   300
gtacatgtag aaattccttg agaggaagac agagagtgac agaatccagg acgttcatgg   360
c                                                                   361

<210> SEQ ID NO 40
<211> LENGTH: 359
<212> TYPE: DNA
<213> ORGANISM: Homo sapiens

<400> SEQUENCE: 40
tcctcactgg gaaacatgag gaatgacccc gtgtgttccc agctgcttgg gtcacctttc    60
tgagccctga tgaggccttt cccgattgag tccoctgaca gatcctatgt aaggacctgt   120
ggcgcaatcc cctgcaatac tacaaggaga tgaagccacc tgaagaggga acagagacgt   180
caggtgagcc gttagttggc actggagctg tttgatgcgc agtataaggg ggttgacaca   240
cctgcctatt cagggagcct gggtgctcat ttcagaaatg tagaaactga ggctcctttc   300
gtacatgtag aaattccttg agaggaagac agagtgacag aatccaggac gttcatggc   359

<210> SEQ ID NO 41
<211> LENGTH: 361
<212> TYPE: DNA
<213> ORGANISM: Homo sapiens

<400> SEQUENCE: 41
tcctcactgg gaaacatgag gaatgacccc gtgtgttccc agctgcttgg gtcacctttc    60
tgagccctga tgaggccttt cccgattgag tccoctgaca gatcctatgt aaggacctgt   120
ggcgcaatcc cctgcaatac tacaaggaga tgaagccacc tgaagaggga acagagacgt   180
caggtgagcc gttagttggc actggagctg tttgatgccc agtataaggg ggttgacaca   240
cctgcctatt cagggagcct gggtgctcat ttcagaaatg tagaaattga ggctcctttc   300
gtacatgtag aaattccttg agaggaagac agagagtgac agaatccagg acgttcatgg   360
c                                                                   361

<210> SEQ ID NO 42
<211> LENGTH: 361
<212> TYPE: DNA
<213> ORGANISM: Homo sapiens

<400> SEQUENCE: 42
tcctcactgg gaaacatgag gaatgacccc gtgtgttccc agctgcttgg gtcacctttc    60
tgagccctga tgaggccttt cccgattgag tccoctgaca gatcctatgt aaggacctgt   120
ggcgcaatcc cctgcaatac tacaaggaga tgaagccacc tgaagaggga acagagacgt   180
caggtgagcc gttagttggc actggagctg tttgatgccc agtataaggg ggttgacaca   240
cctgcctatt cagggagcct gggtgctcat ttcagaaatg tagaaattga ggctcctttc   300
```

-continued gtacatgtag aaattccttg agaggaagac agagagtgac agaatccagg acgttcatgg    360
c    361

<210> SEQ ID NO 43
<211> LENGTH: 361
<212> TYPE: DNA
<213> ORGANISM: Homo sapiens

<400> SEQUENCE: 43
tcctcactgg gaaacatgag gaatgacccc gtgtgttccc agctgcttgg gtcacctttc    60
tgagccctga tgaggccttt cccgattgag tccctgaca gatcctatgt aaggacctgt    120
ggcgcaatcc cctgcaatac tacaagagga tgaagccacc tgaagaggga acagagacgt    180
caggtgagcc gttagttggc actggagctg tttgatgccc agtataaggg ggttgacaca    240
cctgcctatt cagggagcct gggtgctcat ttcagaaatg tagaaattga ggctcctttc    300
gtacatgtag aaattccttg agaggaagac agagagtgac agaatccagg acgttcatgg    360
c    361

<210> SEQ ID NO 44
<211> LENGTH: 361
<212> TYPE: DNA
<213> ORGANISM: Homo sapiens

<400> SEQUENCE: 44
tcctcactgg gaaacatgag gaatgacccc atgtgttccc agctgcttgg gtcacctttc    60
tgagccctga tgaggccttt cccgattgag tccctgaca gatcctatgt aaggacctgt    120
ggcgcaatcc cctgcaatac tacaagagga tgaagccacc tgaagaggga acagagacgt    180
caggtgagcc gttagttggc actggagctg tttgatgccc agtataaggg ggttgacaca    240
cctgcctatt cagggagcct gggtgctcat ttcagaaatg tagaaattga ggctcctttc    300
gtacatgtag aaattccttg agaggaagac agagagtgac agaatccagg acgttcatgg    360
c    361

<210> SEQ ID NO 45
<211> LENGTH: 361
<212> TYPE: DNA
<213> ORGANISM: Homo sapiens

<400> SEQUENCE: 45
tcctcactgg gaaacatgag gaatgacccc gtgtgttccc agctgcttgg gtcacctttc    60
tgagccctga tgaggccttt cccgattgag tccctgaca gatcctatgt aaggacctgt    120
ggcgcaatcc cctgcaatac tacaagagga tgaagccacc tgaagaggga acagagacgt    180
caggtgagcc gttagttggc actggagctg tttgatgccc agtataaggg ggttgacaca    240
cctgcctatt cagggagcct gggtgctcat ttcagaaatg tagaaattga ggctcctttc    300
gtacatgtag aaattccttg agaggaagac agagagtgac agaatccagg acgttcatgg    360
c    361

METHOD FOR QUANTIFYING AND/OR DETECTING HUMAN MALE DNA

FIELD OF THE INVENTION

The present invention is in the field of molecular biology, diagnostics, more particularly in the field of analytical and forensic sciences. The invention is further in the field of nucleic acid amplification and quantification, more particularly in the field of DNA quantification.

BACKGROUND OF THE INVENTION

The determination of the quantity of DNA recovered from forensic samples as well as other samples is a critical step in the overall DNA typing process, but also in the detection of DNA in various other fields of science. A narrow range of input DNA from 0.5 to 2 ng is often needed to produce optimal results with for example multiplex DNA typing kits. Therefore, in order to ensure that a positive result is a positive result and/or a negative result is a negative result due to the absence of DNA, quantification of DNA is of absolute importance. Furthermore, the quality of standards for forensic DNA testing laboratories requires human-specific DNA quantification. This is due to isolation techniques that can recover human DNA as well as bacterial and other exogenous DNA. A number of procedures have been developed to permit quantification of human-specific DNA including start-blot techniques, liquid based hybridization assays and real-time polymerase chain reaction (PCR). Currently, real-time PCR is the dominant technique due to its wide dynamic range and ease of automation.

The modern short tandem repeat (STR) kits have become much more sensitive and can obtain good results even using low amounts of DNA. Therefore, there is a desire for a method, kit and nucleic acid region that allows precise and accurate quantification of human DNA even in low concentrated samples.

There are certain quantification and detection kits already available. One such kit is the Quantifiler Human Kit (Applied Biosystems) another kit is Quantifiler Duo Kit (Applied Biosystems) another kit is the Plexor HY Real-Time PCR Quantification Kit (Promega). Both the Quantifiler Duo Kit and the Plexor HY Kit target an autosomal and a gonosomal (Y-chromosome) target on the genome.

However, the kits currently on the market present some drawbacks. According to LaSalle et al. (Forensic Science International: Genetics, (2011) 5: 185-193) the Quantifiler Kits are more accurate in the quantification but have a lower dynamic range as the Plexor HY. The Plexor HY offers a higher dynamic range due to the amplification of a multicopy target, but a lower accuracy. This lower accuracy can be attributed to the multicopy target. If less than the full set of 20 copies on a genome amplify, because of, for example, instability in the target copy number, than the ratio between the amplification between autosomal and gonosomal (Y) target may vary. The dynamic range of the Plexor HY kit is slightly better than that of the other kit (LaSalle et al., Forensic Science International: Genetics, (2011) 5: 185-193). In a statistical comparison, it has been demonstrated a significant difference between the two kits (LaSalle et al., Forensic Science International: Genetics, (2011) 5: 185-193).

Another important parameter in forensics is the degradation grade of the DNA that has to be analyzed. Since the amplicon size of the Quantifiler Human and Plexor HY vary from 62 to 133 base pairs (bp), significant differences might be expected when the kits are applied to degraded DNA. Also, inhibitors must be taken into account. It may well be that DNA is present in the reaction no result is obtained due to the presence of inhibitory substances.

In cases of sexual assault samples, a quantification of the DNA is challenging, due to the presence of DNA molecules from both, the female victim as well as the male attacker. Furthermore, in a typical sample, the amount of female DNA exceeds the amount of male DNA by several orders of magnitude. Thus, a sensitive, male specific DNA quantification method which can accurately detect and quantify male DNA even in a high background of female DNA, is therefore of great interest.

Reported herein is a qPCR-based DNA quantification system that is highly sensitive to detect low amounts of male DNA in a high background of female DNA and assess in parallel the male DNA degradation and/or integrity of the male DNA.

SUMMARY OF THE INVENTION

The invention relates to a method for detecting and/or quantifying DNA, in particular the fraction of male DNA in a sample, (i) wherein the method comprises the step of amplification of a multicopy locus within the Y-chromosome (MCL-Y), wherein said locus shares at least 85% sequence identity to a sequence according to SEQ ID NO. 3 over a stretch of at least 60 base pairs (bp) or with the reverse complement thereof or, (ii) wherein the locus is amplifiable with a primer pair according to SEQ ID NO. 1 and 2 or the reverse complement thereof.

A second aspect of the present invention relates to a primer or primer pair wherein at least one primer hybridizes under stringent conditions to a sequence according to SEQ ID NO 3. Preferably, both primers of the primer pair hybridize.

A third aspect of the present invention relates to a kit for performing a method according to any of the claims 1 to 10, wherein said kit comprises: a. at least one primer selected from the group consisting of: SEQ ID NO 1 and SEQ ID NO 2; b. reagents to perform the amplification reaction; c. instructions for performing the method according to any of the claims 1 to 10.

Maternal blood stream contains low amounts of cell-free fetal DNA (cffDNA) which is freely circulating. Analysis of cffDNA provides a method of non-invasive prenatal diagnosis, testing and can be used e.g. for early determination of fetal sex. The present method also enables the detection and analysis of male cell-free fetal DNA and aids in identification of fetal sex. Furthermore the present method significantly decreases the risk of false sex determination of the embryo since contaminating male genomic DNA, e.g. introduced into the sample from the environment, can be assessed by the Degradation Index generated by the small and large PCR system for the male targets used in the invention.

DESCRIPTION OF THE INVENTION

In case of forensic samples from sexual assaults the female DNA usually exceeds the amount of male DNA. To choose the proper method for genetic analysis it is advisable to test for male DNA present in the sample, which was collected from a crime scene and to quantify the amount of male DNA in order to know how much of this DNA should be used in the genetic analysis e.g. STR reaction. The typical STR kit detects genetic length polymorphisms on different autosomal chromosomes, but in some cases, such as with sexual assault samples, the analysis of length polymorphisms exclusively on the Y-chromosome could be advantageous, because the female DNA does not contain these length polymorphisms.

Surprisingly, the inventors have found that multicopy loci on the Y-chromosome are superior to other loci when used for detection and/or quantification of nucleic acids, because the sensitivity of the reaction can be enhanced. This is an important aspect of the present invention due to its relevancy in the field of forensic science.

In particular, the inventors have astonishingly found that sequence identified in SEQ ID NO. 3 and/or sequences that share sequence similarity, i.e. SEQ ID NO. 4 with it may be found many times on the Y-chromosome. In particular, said sequence SEQ ID NO. 3 or sequences very similar thereto are present nine times on the human Y-chromosome. This finding provides a valuable advantage of the present method.

The invention relates to a method for detecting and/or quantifying DNA in particular the fraction of male DNA in a sample, (i) wherein the method comprises the step of amplification of a multicopy locus within the Y-chromosome (MCL-Y), wherein said locus shares at least 85% sequence identity to a sequence according to SEQ ID NO. 3 over a stretch of at least 60 base pairs (bp) or with the reverse complement thereof or, (ii) wherein the locus is amplifiable with a primer pair according to SEQ ID NO. 1 and 2 or the reverse complement thereof.

In the context of the present invention, the term "amplifiable" refers to the property of a locus of being amplified by any amplification method. A person skilled in the art knows that the achievement of the amplification reaction depends on the experimental condition used.

The invention relates to a method, wherein the amplification step is performed using at least one primer selected from one of the groups consisting of (i) SEQ ID NO. 1 and SEQ ID NO. 2, (ii) a reverse complement of SEQ ID NO. 1 and SEQ ID NO. 2 and (iii) a primer that shares at least 90% sequence identity with one of the primers with SEQ ID NO. 1 and SEQ ID NO. 2 or a reverse complement thereof.

| | |
|---|---|
| SEQ ID NO. 1<br>Downstream<br>primer 81 bp<br>fragment | 5'GAAAGGCCTCATCAGGGCTCAG 3' |
| SEQ ID NO. 2<br>Upstream<br>primer | 5'TCCTCACTGGGAAACATGAGGAATGAC 3' |

The invention relates to a method, wherein the amplification step is performed using a primer pair selected from one of the groups consisting of (i) SEQ ID NO. 1 and SEQ ID NO. 2, (ii) a reverse complement of SEQ ID NO. 1 and SEQ ID NO. 2 and (iii) a primer that shares at least 90% sequence identity with one of the primers with SEQ ID NO. 1 and SEQ ID NO. 2 or a reverse complement thereof.

The sequences distributed throughout the genome are not all exactly identical. It is important that the selected primers bind also to the nearly identical sequences. Thus, ideally the locus shares at least 60%, 70%, 80%, 90% or even 95% or 98% sequence identity to a sequence according to SEQ ID NO. 3 over a stretch of 60 bp.

The locus may also be chosen from any of SEQ ID NO. 3 to 11. Thus, if SEQ ID NO. 3 is claimed herein the same applies to 4 to 11.

| | |
|---|---|
| SEQ ID NO. 3<br>(chrY:9529589-<br>9529669 81 bp) | 5'GAAAGGCCTCATCAGGGCTCAGaaaggtgacccaagca<br>gctgggaacacacgggGTCATTCCTCATGTTTCCCAGTGA<br>GGA 3' |
| SEQ ID NO. 4<br>(chrY:9509276-<br>9509356 81 bp) | 5'GAAAGGCCTCATCAGGGCTCAGaaaggtgacccaagca<br>gctgggaacacacgggGTCATTCCTCATGTTTCCCAGTGA<br>GGA 3' |
| SEQ ID NO. 5<br>(chrY:9488994-<br>9489074 81 bp) | 5'GAAAGGCCTCATCAGGGCTCAGaaaggtgacccaagca<br>gctgggaacacatgggGTCATTCCTCATGTTTCCCAGTGA<br>GGA 3' |
| SEQ ID NO. 6<br>(chrY:9468664-<br>9468744 81 bp) | 5'GAAAGGCCTCATCAGGGCTCAGaaaggtgacccaagca<br>gctgggaacacacgggGTCATTCCTCATGTTTCCCAGTGA<br>GGA 3' |
| SEQ ID NO. 7<br>(chrY:9400130-<br>9400210 81 bp) | 5'GAAAGGCCTCATCAGGGCTCAGaaaggtgacccaagca<br>gctgggaacacacgggGTCATTCCTCATGTTTCCCAGTGA<br>GGA 3' |
| SEQ ID NO. 8<br>(chrY:9379784-<br>9379864 81 bp) | 5'GAAAGGCCTCATCAGGGCTCAGaaaggtgacccaagca<br>gctgggaacacacgggGTCATTCCTCATGTTTCCCAGTGA<br>GGA 3' |
| SEQ ID NO. 9<br>(chrY:9359506-<br>9359586 81 bp) | 5'GAAAGGCCTCATCAGGGCTCAGaaaggtgacccaagca<br>gctgggaacacacgggGTCATTCCTCATGTTTCCCAGTGA<br>GGA 3' |
| SEQ ID NO. 10<br>(chrY:9339191-<br>9339271 81 bp) | 5'GAAAGGCCTCATCAGGGCTCAGaaaggtgacccaagca<br>gctgggaacacatgggGTCATTCCTCATGTTTCCCAGTGA<br>GGA 3' |
| SEQ ID NO. 11<br>(chrY:6247926-<br>6248006 81 bp) | 5'GAAAGGCCTCATCAGGGCTCAGaaaggtgacccaagca<br>gctgggaacacacgggGTCATTCCTCATGTTTCCCAGTGA<br>GGA 3' |
| SEQ ID NO. 12<br>Probe for 81 bp<br>fragment | 5' ggtgacccaagcagctgggaacaca 3' |

-continued

| | |
|---|---|
| SEQ ID NO. 13<br>Downstream primer<br>no. 3 | 5' CATGAACGTCCTGGATTCTGTCACTC 3' |
| SEQ ID NO. 14<br>Downstream primer<br>no. 4 | 5' TCACTCTCTGTCTTCCTCTCAAGGAATTTCTAC 3' |
| SEQ ID NO. 15<br>Downstream primer<br>no. 5 | 5' GCCATGAACGTCCTGGATTCTGTCAC 3' |
| SEQ ID NO. 16<br>Probe for larger<br>fragment | 5' CAGGCTCCCTGAATAGGCAGGTGTG 3' |
| SEQ ID NO: 17<br>(Upstream primer<br>SEQ ID NO. 2 and<br>Downstream primer<br>SEQ ID NO. 13-<br>Locus:chrY:9529589 +<br>9529947) | 5' TCCTCACTGGGAAACATGAGGAATGACcccgtgtgttc<br>ccagctgcttgggtcacctttctgagccctgatgaggcct<br>ttcccgattgagtcccctgacagatcctatgtaaggacct<br>gtggcgcaatcccctgcaatactacaagaggatgaagcca<br>cctgaagagggaacagagacgtcaggtgagccgttagttg<br>gcactggagctgtttgatgcccagtataaggggggttgaca<br>cacctgcctattcagggagcctgggtgctcatttcagaaa<br>tgtagaaattgaggctcctttcgtacatgtagaaattcct<br>tgagaggaagacagaGAGTGACAGAATCCAGGACGTTCAT<br>G 3' |
| SEQ ID NO. 18<br>(Upstream primer<br>SEQ ID NO. 2 and<br>Downstream primer<br>SEQ ID NO. 13<br>Locus:chrY:9509276 +<br>9509634) | 5'TCCTCACTGGGAAACATGAGGAATGACcccgtgtgttc<br>ccagctgcttgggtcacctttctgagccctgatgaggcct<br>ttcccgattgagtcccctgacagatcctatgtaaggacct<br>gtggcgcaatcccctgcaatactacaagaggatgaagcca<br>cctgaagagggaacagagacgtcaggtgagccgttagttg<br>gcactggagctgtttgatgcccagtataaggggggttgaca<br>cacctgcctattcagggagcctgggtgctcatttcagaaa<br>tgtagaaattgaggctcctttcgtacatgtagaaattcct<br>tgagaggaagacagaGAGTGACAGAATCCAGGACGTTCAT<br>G 3' |
| SEQ ID NO. 19<br>(Upstream primer<br>SEQ ID NO. 2 and<br>Downstream primer<br>SEQ ID NO. 13<br>Locus:chrY:9488994 +<br>9489352) | 5'TCCTCACTGGGAAACATGAGGAATGACcccatgtgttc<br>ccagctgcttgggtcacctttctgagccctgatgaggcct<br>ttcccgattgagtcccctgacagatcctatgtaaggacct<br>gtggcgcaatcccctgcaatactacaagaggatgaagcca<br>cctgaagagggaacagagacgtcaggtgagccgttagttg<br>gcactggagctgtttgatgcccagtataaggggggttgaca<br>cacctgcctattcagggagcctgggtgctcatttcagaaa<br>tgtagaaattgaggctcctttcgtacatgtagaaattcct<br>tgagaggaagacagaGAGTGACAGAATCCAGGACGTTCAT<br>G 3' |
| SEQ ID NO. 20<br>(Upstream primer<br>SEQ ID NO. 2 and<br>Downstream primer<br>SEQ ID NO. 13<br>Locus:chrY:9468664 +<br>9469020) | 5'TCCTCACTGGGAAACATGAGGAATGACcccgtgtgttc<br>ccagctgcttgggtcacctttctgagccctgatgaggcct<br>ttcccgattgagtcccctgacagatcctatgtaaggacct<br>gtggcgcaatcccctgcaatactacaagaggatgaagcca<br>cctgaagagggaacagagacgtcaggtgagccgttagttg<br>gcactggagctgtttgatgcgcagtataagggggttgaca<br>cacctgcctattcagggagcctgggtgctcatttcagaaa<br>tgtagaaactgaggctcctttcgtacatgtagaaattcct<br>tgagaggaagacaGAGTGACAGAATCCAGGACGTTCATG<br>3' |
| SEQ ID NO. 21<br>(Upstream primer<br>SEQ ID NO. 2 and<br>Downstream primer<br>SEQ ID NO. 13<br>Locus:chrY:9400130 +<br>9400488) | 5'TCCTCACTGGGAAACATGAGGAATGACcccgtgtgttc<br>ccagctgcttgggtcacctttctgagccctgatgaggcct<br>ttcccgattgagtcccctgacagatcctatgtaaggacct<br>gtggcgcaatcccctgcaatactacaagaggatgaagcca<br>cctgaagagggaacagagacgtcaggtgagccgttagttg<br>gcactggagctgtttgatgcccagtataaggggggttgaca<br>cacctgcctattcagggagcctgggtgctcatttcagaaa<br>tgtagaaattgaggctcctttcgtacatgtagaaattcct<br>tgagaggaagacagaGAGTGACAGAATCCAGGACGTTCAT<br>G 3' |
| SEQ ID NO. 22<br>(Upstream primer<br>SEQ ID NO. 2 and<br>Downstream primer<br>SEQ ID NO. 13<br>Locus:chrY:9379784 +<br>9380142) | 5'TCCTCACTGGGAAACATGAGGAATGACcccgtgtgttc<br>ccagctgcttgggtcacctttctgagccctgatgaggcct<br>ttcccgattgagtcccctgacagatcctatgtaaggacct<br>gtggcgcaatcccctgcaatactacaagaggatgaagcca<br>cctgaagagggaacagagacgtcaggtgagccgttagttg<br>gcactggagctgtttgatgcccagtataaggggggttgaca<br>cacctgcctattcagggagcctgggtgctcatttcagaaa |

-continued

| | |
|---|---|
| | tgtagaaattgaggctcctttcgtacatgtagaaattcct<br>tgagaggaagacagaGAGTGACAGAATCCAGGACGTTCAT<br>G 3' |
| SEQ ID NO. 23<br>(Upstream primer<br>SEQ ID NO. 2 and<br>Downstream primer<br>SEQ ID NO. 13<br>Locus:chrY:9359506 +<br>9359864 | 5'TCCTCACTGGGAAACATGAGGAATGACcccgtgtgttc<br>ccagctgcttgggtcacctttctgagccctgatgaggcct<br>ttcccgattgagtcccctgacagatcctatgtaaggacct<br>gtggcgcaatcccctgcaatactacaagaggatgaagcca<br>cctgaagagggaacagagacgtcaggtgagccgttagttg<br>gcactggagctgtttgatgcccagtataaggggggttgaca<br>cacctgcctattcagggagcctgggtgctcatttcagaaa<br>tgtagaaattgaggctcctttcgtacatgtagaaattcct<br>tgagaggaagacagaGAGTGACAGAATCCAGGACGTTCAT<br>G 3' |
| SEQ ID NO. 24<br>(Upstream primer<br>SEQ ID NO. 2 and<br>Downstream primer<br>SEQ ID NO. 13<br>Locus:chrY:9339191 +<br>9339549) | 5'TCCTCACTGGGAAACATGAGGAATGACcccatgtgttc<br>ccagctgcttgggtcacctttctgagccctgatgaggcct<br>ttcccgattgagtcccctgacagatcctatgtaaggacct<br>gtggcgcaatcccctgcaatactacaagaggatgaagcca<br>cctgaagagggaacagagacgtcaggtgagccgttagttg<br>gcactggagctgtttgatgcccagtataagggggttgaca<br>cacctgcctattcagggagcctgggtgctcatttcagaaa<br>tgtagaaattgaggctcctttcgtacatgtagaaattcct<br>tgagaggaagacagaGAGTGACAGAATCCAGGACGTTCAT<br>G 3' |
| SEQ ID NO. 25<br>(Upstream primer<br>SEQ ID NO. 2 and<br>Downstream primer<br>SEQ ID NO. 13<br>Locus:chrY:6247926 +<br>6248284) | 5'TCCTCACTGGGAAACATGAGGAATGACcccatgtgttc<br>ccagctgcttgggtcacctttctgagccctgatgaggcct<br>ttcccgattgagtcccctgacagatcctatgtaaggacct<br>gtggcgcaatcccctgcaatactacaagaggatgaagcca<br>cctgaagagggaacagagacgtcaggtgagccgttagttg<br>gcactggagctgtttgatgcccagtataagggggttgaca<br>cacctgcctattcagggagcctgggtgctcatttcagaaa<br>tgtagaaattgaggctcctttcgtacatgtagaaattcct<br>tgagaggaagacagaGAGTGACAGAATCCAGGACGTTCAT<br>G 3' |
| SEQ ID NO. 26<br>(Upstream primer<br>SEQ ID NO. 2 and<br>Downstream primer<br>SEQ ID NO. 14<br>Locus:<br>chrY:9549757 +<br>9550096) | 5'TCCTCACTGGGAAACATGAGGAATGACcccgtgtgttc<br>ccagctgcttgggtcaccattctgagtcctgatgaggcct<br>ttcccgatggattcccctgacagatcctatgtaaggacct<br>gtggtgcaatcccctgcaatcctacaagaggatgaagcca<br>cctgaagagggaacagagatttcaggtgagctgttcagtt<br>ggaactgaagcttttgatccccaggataaggaggttgac<br>acacctgcctattcagggagcctggaggctcatttcagaa<br>atgtagaaattgagcctcctttcatacatGTAGAAATTCC<br>TTGAGAGGAAGACAGAGtGTGA 3' |
| SEQ ID NO. 27<br>(Upstream primer<br>SEQ ID NO. 2 and<br>Downstream primer<br>SEQ ID NO. 14<br>Locus:chrY:9529589 +<br>9529927 | 5'TCCTCACTGGGAAACATGAGGAATGACcccgtgtgttc<br>ccagctgcttgggtcacctttctgagccctgatgaggcct<br>ttcccgattgagtcccctgacagatcctatgtaaggacct<br>gtggcgcaatcccctgcaatactacaagaggatgaagcca<br>cctgaagagggaacagagacgtcaggtgagccgttagttg<br>gcactggagctgtttgatgcccagtataagggggttgaca<br>cacctgcctattcagggagcctgggtgctcatttcagaaa<br>tgtagaaattgaggctcctttcgtacatGTAGAAATTCCT<br>TGAGAGGAAGACAGAGAGTGA 3' |
| SEQ ID NO. 28<br>(Upstream primer<br>SEQ ID NO. 2 and<br>Downstream primer<br>SEQ ID NO. 14<br>Locus:chrY:9509276 +<br>9509614) | 5'TCCTCACTGGGAAACATGAGGAATGACcccgtgtgttc<br>ccagctgcttgggtcacctttctgagccctgatgaggcct<br>ttcccgattgagtcccctgacagatcctatgtaaggacct<br>gtggcgcaatcccctgcaatactacaagaggatgaagcca<br>cctgaagagggaacagagacgtcaggtgagccgttagttg<br>gcactggagctgtttgatgcccagtataagggggttgaca<br>cacctgcctattcagggagcctgggtgctcatttcagaaa<br>tgtagaaattgaggctcctttcgtacatGTAGAAATTCCT<br>TGAGAGGAAGACAGAGAGTGA 3' |
| SEQ ID NO. 29<br>(Upstream primer<br>SEQ ID NO. 2 and<br>Downstream primer<br>SEQ ID NO. 14<br>Locus:chrY:9488994 +<br>9489332) | 5'TCCTCACTGGGAAACATGAGGAATGACcccatgtgttc<br>ccagctgcttgggtcacctttctgagccctgatgaggcct<br>ttcccgattgagtcccctgacagatcctatgtaaggacct<br>gtggcgcaatcccctgcaatactacaagaggatgaagcca<br>cctgaagagggaacagagacgtcaggtgagccgttagttg<br>gcactggagctgtttgatgcccagtataagggggttgaca<br>cacctgcctattcagggagcctgggtgctcatttcagaaa<br>tgtagaaattgaggctcctttcgtacatGTAGAAATTCCT<br>TGAGAGGAAGACAGAGAGTGA 3' |

| | |
|---|---|
| SEQ ID NO. 30<br>(Upstream primer<br>SEQ ID NO. 2 and<br>Downstream primer<br>SEQ ID NO. 14<br>Locus:chrY:9468664 +<br>9469002) | 5'TCCTCACTGGGAAACATGAGGAATGACcccgtgtgttc<br>ccagctgcttgggtcacctttctgagccctgatgaggcct<br>ttcccgattgagtccctgacagatcctatgtaaggacct<br>gtggcgcaatcccctgcaatactacaagaggatgaagcca<br>cctgaagagggaacagagacgtcaggtgagccgttagttg<br>gcactggagctgtttgatgcgcagtataaggggggttgaca<br>cacctgcctattcagggagcctgggtgctcatttcagaaa<br>tgtagaaactgaggctcctttcgtacatGTAGAAATTCCT<br>TGAGAGGAAGACAGAGtGacA 3' |
| SEQ ID NO. 31<br>(Upstream primer<br>SEQ ID NO. 2 and<br>Downstream primer<br>SEQ ID NO. 14<br>Locus:chrY:9400130 +<br>9400468) | 5'TCCTCACTGGGAAACATGAGGAATGACcccgtgtgttc<br>ccagctgcttgggtcacctttctgagccctgatgaggcct<br>ttcccgattgagtccctgacagatcctatgtaaggacct<br>gtggcgcaatcccctgcaatactacaagaggatgaagcca<br>cctgaagagggaacagagacgtcaggtgagccgttagttg<br>gcactggagctgtttgatgcccagtataaggggggttgaca<br>cacctgcctattcagggagcctgggtgctcatttcagaaa<br>tgtagaaattgaggctcctttcgtacatGTAGAAATTCCT<br>TGAGAGGAAGACAGAGAGTGA 3' |
| SEQ ID NO. 32<br>(Upstream primer<br>SEQ ID NO. 2 and<br>Downstream primer<br>SEQ ID NO. 14<br>Locus:chrY:9379784 +<br>9380122) | 5'TCCTCACTGGGAAACATGAGGAATGACcccgtgtgttc<br>ccagctgcttgggtcacctttctgagccctgatgaggcct<br>ttcccgattgagtccctgacagatcctatgtaaggacct<br>gtggcgcaatcccctgcaatactacaagaggatgaagcca<br>cctgaagagggaacagagacgtcaggtgagccgttagttg<br>gcactggagctgtttgatgcccagtataaggggggttgaca<br>cacctgcctattcagggagcctgggtgctcatttcagaaa<br>tgtagaaattgaggctcctttcgtacatGTAGAAATTCCT<br>TGAGAGGAAGACAGAGAGTGA 3' |
| SEQ ID NO. 33<br>(Upstream primer<br>SEQ ID NO. 2 and<br>Downstream primer<br>SEQ ID NO. 14<br>Locus:chrY:9359506 +<br>9359844) | 5'TCCTCACTGGGAAACATGAGGAATGACcccgtgtgttc<br>ccagctgcttgggtcacctttctgagccctgatgaggcct<br>ttcccgattgagtccctgacagatcctatgtaaggacct<br>gtggcgcaatcccctgcaatactacaagaggatgaagcca<br>cctgaagagggaacagagacgtcaggtgagccgttagttg<br>gcactggagctgtttgatgcccagtataaggggggttgaca<br>cacctgcctattcagggagcctgggtgctcatttcagaaa<br>tgtagaaattgaggctcctttcgtacatGTAGAAATTCCT<br>TGAGAGGAAGACAGAGAGTGA 3' |
| SEQ ID NO. 34<br>(Upstream primer<br>SEQ ID NO. 2 and<br>Downstream primer<br>SEQ ID NO. 14<br>Locus:chrY:9339191 +<br>9339529) | 5'TCCTCACTGGGAAACATGAGGAATGACcccatgtgttc<br>ccagctgcttgggtcacctttctgagccctgatgaggcct<br>ttcccgattgagtccctgacagatcctatgtaaggacct<br>gtggcgcaatcccctgcaatactacaagaggatgaagcca<br>cctgaagagggaacagagacgtcaggtgagccgttagttg<br>gcactggagctgtttgatgcccagtataaggggggttgaca<br>cacctgcctattcagggagcctgggtgctcatttcagaaa<br>tgtagaaattgaggctcctttcgtacatGTAGAAATTCCT<br>TGAGAGGAAGACAGAGAGTGA 3' |
| SEQ ID NO. 35<br>(Upstream primer<br>SEQ ID NO. 2 and<br>Downstream primer<br>SEQ ID NO. 14<br>Locus:chrY:6247926 +<br>6248264) | 5'TCCTCACTGGGAAACATGAGGAATGACcccgtgtgttc<br>ccagctgcttgggtcacctttctgagccctgatgaggcct<br>ttcccgattgagtccctgacagatcctatgtaaggacct<br>gtggcgcaatcccctgcaatactacaagaggatgaagcca<br>cctgaagagggaacagagacgtcaggtgagccgttagttg<br>gcactggagctgtttgatgcccagtataaggggggttgaca<br>cacctgcctattcagggagcctgggtgctcatttcagaaa<br>tgtagaaattgaggctcctttcgtacatGTAGAAATTCCT<br>TGAGAGGAAGACAGAGAGTGA 3' |
| SEQ ID NO. 36<br>(Upstream primer<br>SEQ ID NO. 2 and<br>Downstream primer<br>SEQ ID NO. 15<br>Locus:chrY:9549757 +<br>9550118) | 5'TCCTCACTGGGAAACATGAGGAATGACcccatgtgttc<br>ccagctgcttgggtcaccattctgagtcctgatgaggcct<br>ttcccgatggattccctgacagatcctatgtaaggacct<br>gtggtgcaatcccctgcaatcctacaagaggatgaagcca<br>cctgaagagggaacagagatttcaggtgagctgttcagtt<br>ggaactgaagcttttttgatcccaggataaggaggttgac<br>acacctgcctattcagggagcctggaggctcatttcagaa<br>atgtagaaattgagcctcctttcatacatgtagaaattcc<br>ttgagaggaagacagagtGTGACAGAATCCAGGACaTTCA<br>TGGC 3' |

-continued

| | |
|---|---|
| SEQ ID NO. 37<br>(Upstream primer<br>SEQ ID NO. 2 and<br>Downstream primer<br>SEQ ID NO. 15<br>Locus:chrY:9529589 +<br>9529949) | 5'TCCTCACTGGGAAACATGAGGAATGACcccgtgtgttc<br>ccagctgcttgggtcacctttctgagccctgatgaggcct<br>ttcccgattgagtcccctgacagatcctatgtaaggacct<br>gtggcgcaatcccctgcaatactacaagaggatgaagcca<br>cctgaagagggaacagagacgtcaggtgagccgttagttg<br>gcactggagctgtttgatgcccagtataaggggggttgaca<br>cacctgcctattcagggagcctgggtgctcatttcagaaa<br>tgtagaaattgaggctcctttcgtacatgtagaaattcct<br>tgagaggaagacagagaGTGACAGAATCCAGGACGTTCAT<br>GGC 3' |
| SEQ ID NO. 38<br>(Upstream primer<br>SEQ ID NO. 2 and<br>Downstream primer<br>SEQ ID NO. 15<br>Locus:chrY:9509276 +<br>9509636) | 5'TCCTCACTGGGAAACATGAGGAATGACcccgtgtgttc<br>ccagctgcttgggtcacctttctgagccctgatgaggcct<br>ttcccgattgagtcccctgacagatcctatgtaaggacct<br>gtggcgcaatcccctgcaatactacaagaggatgaagcca<br>cctgaagagggaacagagacgtcaggtgagccgttagttg<br>gcactggagctgtttgatgcccagtataaggggggttgaca<br>cacctgcctattcagggagcctgggtgctcatttcagaaa<br>tgtagaaattgaggctcctttcgtacatgtagaaattcct<br>tgagaggaagacagagaGTGACAGAATCCAGGACGTTCAT<br>GGC 3' |
| SEQ ID NO. 39<br>(Upstream primer<br>SEQ ID NO. 2 and<br>Downstream primer<br>SEQ ID NO. 15<br>Locus:chrY:9488994 +<br>9489354) | 5'TCCTCACTGGGAAACATGAGGAATGACcccatgtgttc<br>ccagctgcttgggtcacctttctgagccctgatgaggcct<br>ttcccgattgagtcccctgacagatcctatgtaaggacct<br>gtggcgcaatcccctgcaatactacaagaggatgaagcca<br>cctgaagagggaacagagacgtcaggtgagccgttagttg<br>gcactggagctgtttgatgcccagtataaggggggttgaca<br>cacctgcctattcagggagcctgggtgctcatttcagaaa<br>tgtagaaattgaggctcctttcgtacatgtagaaattcct<br>tgagaggaagacagagaGTGACAGAATCCAGGACGTTCAT<br>GGC 3' |
| SEQ ID NO. 40<br>(Upstream primer<br>SEQ ID NO. 2 and<br>Downstream primer<br>SEQ ID NO. 15<br>Locus:chrY:9468664 +<br>9469022) | 5'TCCTCACTGGGAAACATGAGGAATGACcccgtgtgttc<br>ccagctgcttgggtcacctttctgagccctgatgaggcct<br>ttcccgattgagtcccctgacagatcctatgtaaggacct<br>gtggcgcaatcccctgcaatactacaagaggatgaagcca<br>cctgaagagggaacagagacgtcaggtgagccgttagttg<br>gcactggagctgtttgatgcgcagtataaggggggttgaca<br>cacctgcctattcagggagcctgggtgctcatttcagaaa<br>tgtagaaactgaggctcctttcgtacatgtagaaattcct<br>tgagaggaagacagagaGTGACAGAATCCAGGACGTTCATGG<br>C 3' |
| SEQ ID NO. 41<br>(Upstream primer<br>SEQ ID NO. 2 and<br>Downstream primer<br>SEQ ID NO. 15<br>Locus:chrY:9400130 +<br>9400490) | 5'TCCTCACTGGGAAACATGAGGAATGACcccgtgtgttc<br>ccagctgcttgggtcacctttctgagccctgatgaggcct<br>ttcccgattgagtcccctgacagatcctatgtaaggacct<br>gtggcgcaatcccctgcaatactacaagaggatgaagcca<br>cctgaagagggaacagagacgtcaggtgagccgttagttg<br>gcactggagctgtttgatgcccagtataaggggggttgaca<br>cacctgcctattcagggagcctgggtgctcatttcagaaa<br>tgtagaaattgaggctcctttcgtacatgtagaaattcct<br>tgagaggaagacagagaGTGACAGAATCCAGGACGTTCAT<br>GGC 3' |
| SEQ ID NO. 42<br>(Upstream primer<br>SEQ ID NO. 2 and<br>Downstream primer<br>SEQ ID NO. 15<br>Locus:chrY:9379784 +<br>9380144) | 5'TCCTCACTGGGAAACATGAGGAATGACcccgtgtgttc<br>ccagctgcttgggtcacctttctgagccctgatgaggcct<br>ttcccgattgagtcccctgacagatcctatgtaaggacct<br>gtggcgcaatcccctgcaatactacaagaggatgaagcca<br>cctgaagagggaacagagacgtcaggtgagccgttagttg<br>gcactggagctgtttgatgcccagtataaggggggttgaca<br>cacctgcctattcagggagcctgggtgctcatttcagaaa<br>tgtagaaattgaggctcctttcgtacatgtagaaattcct<br>tgagaggaagacagagaGTGACAGAATCCAGGACGTTCAT<br>GGC 3' |
| SEQ ID NO. 43<br>(Upstream primer<br>SEQ ID NO. 2 and<br>Downstream primer<br>SEQ ID NO. 15<br>Locus:chrY:9359506 +<br>9359866) | 5'TCCTCACTGGGAAACATGAGGAATGACcccgtgtgttc<br>ccagctgcttgggtcacctttctgagccctgatgaggcct<br>ttcccgattgagtcccctgacagatcctatgtaaggacct<br>gtggcgcaatcccctgcaatactacaagaggatgaagcca<br>cctgaagagggaacagagacgtcaggtgagccgttagttg<br>gcactggagctgtttgatgcccagtataaggggggttgaca<br>cacctgcctattcagggagcctgggtgctcatttcagaaa<br>tgtagaaattgaggctcctttcgtacatgtagaaattcct<br>tgagaggaagacagagaGTGACAGAATCCAGGACGTTCAT<br>GGC 3' |

-continued

| | |
|---|---|
| SEQ ID NO. 44<br>(Upstream primer<br>SEQ ID NO. 2 and<br>Downstream primer<br>SEQ ID NO. 15<br>Locus:chrY:9339191 +<br>9339551) | 5'TCCTCACTGGGAAACATGAGGAATGACcccatgtgttc<br>ccagctgcttgggtcacctttctgagccctgatgaggcct<br>ttcccgattgagtccctgacagatcctatgtaaggacct<br>gtggcgcaatccctgcaatactacaagaggatgaagcca<br>cctgaagagggaacagagacgtcaggtgagccgttagttg<br>gcactggagctgtttgatgcccagtataagggggttgaca<br>cacctgcctattcagggagcctgggtgctcatttcagaaa<br>tgtagaaattgaggctcctttcgtacatgtagaaattcct<br>tgagaggaagacagagaGTGACAGAATCCAGGACGTTCAT<br>GGC 3' |
| SEQ ID NO. 45<br>(Upstream primer<br>SEQ ID NO. 2 and<br>Downstream primer<br>SEQ ID NO. 15<br>Locus:chrY:6247926 +<br>6248286) | 5'TCCTCACTGGGAAACATGAGGAATGACcccgtgtgttc<br>ccagctgcttgggtcacctttctgagccctgatgaggcct<br>ttcccgattgagtccctgacagatcctatgtaaggacct<br>gtggcgcaatccctgcaatactacaagaggatgaagcca<br>cctgaagagggaacagagacgtcaggtgagccgttagttg<br>gcactggagctgtttgatgcccagtataagggggttgaca<br>cacctgcctattcagggagcctgggtgctcatttcagaaa<br>tgtagaaattgaggctcctttcgtacatgtagaaattcct<br>tgagaggaagacagagaGTGACAGAATCCAGGACGTTCAT<br>GGC 3' |

The inventors have astonishingly developed a very versatile system for degradation analysis.

The degradation status/integrity of male DNA can be assessed by using for example, at least two differently sized genomic regions in a qPCR in one vessel. The amplified targets have to have equal amplification efficiencies, causing co-amplification of the targets with the same efficiency. In case of degraded male DNA the mean length of the male DNA fragments in the sample will decrease leading to a loss of efficiency in amplification of the longer PCR systems. The shorter the fragments in the degraded male DNA sample the higher the differences in amplification efficiencies between the shorter and larger PCR systems will become. Hereby, the integrity of male DNA or degradation status of the male DNA can be expressed by a ratio of the quantification of the systems used. The ratio is designated as degradation index. Therefore, in one aspect of the present invention, the status of DNA integrity and/or degradation is expressed by the ratio of the quantification of the at least two overlapping regions within the at least one locus.

Therefore, in one aspect of the present invention, the status of DNA integrity and/or degradation is expressed by the ratio of the quantification of the at least two overlapping regions within the at least one locus.

Here, the smaller fragment is combined with different larger fragments, depending on the extent of degradation of the nucleic acid.

The larger fragment may be a:
(i) 359 bp or 357 bp fragment (primers SEQ ID NO. 2 and SEQ ID NO. 13),
(ii) a 340 bp fragment or a 339 bp fragment (e.g. primers SEQ ID NO. 2 and SEQ ID NO. 14), or a
(iii) 359 bp fragment, 361 bp fragment or a 362 bp fragment (SEQ ID NO. 2 and SEQ ID NO. 15)

Uniquely the system is set-up so that one of the primers in the primer pairs is common to the two or more fragments, being amplified. Thus, the two fragments small and large may have a common up-stream or down-stream primer. Here, it is preferred that the upstream primer (SEQ ID NO. 2) is common to all amplifications.

The determination of percent identity between two sequences is accomplished using the mathematical algorithm of Karlin and Altschul (Proc. Natl. Acad. Sci. USA (1993) 90: 5873-5877). Such an algorithm is the basis of the BLASTN and BLASTP programs of Altschul et al. (J. Mol. Biol. (1990) 215: 403-410). BLAST nucleotide searches are performed with the BLASTN program, score=100, word length=12, to obtain nucleotide sequences homologous SEQ ID NO. 1. To obtain gapped alignments for comparative purposes, Gapped BLAST is utilized as described by Altschul et al. (Nucleic Acids Res. (1997) 25: 3389-3402). When utilizing BLAST and Gapped BLAST programs, the default parameters of the respective programs are used.

The forensic workflow of sexual assault samples suggests the quantification of the male DNA before the STR reaction is carried out. This is done first to help in the decision of which kind of STR Kit has to be used for the genetic analysis, and then to determine how much DNA was obtained from a sample, e.g. collected from a crime scene, and how much of this DNA should be used in a STR reaction. Different STR Kits are available, the typical STR Kit detects genetic length polymorphisms on different autosomal chromosomes, but in some cases, such as with sexual assault samples, the analysis of length polymorphisms exclusively on the Y-chromosome could be advantageous, because the female DNA doesn't have a Y chromosome.

The typical STR reaction works optimally in certain range of template DNA and the whole analysis is very labour-intensive, therefore methodologies are needed that ensure a very high success rate in the STR analysis. Therefore, it is a real advantage if the quantification kit enables the user not only to surely identify the amount of DNA present but also to assess the absence of inhibitors, which could compromise the STR reaction result, which would result in failure or loss of valuable sample material, which could be further purified in case critical inhibition is observed.

According to one embodiment of the present invention, said multicopy locus within the human Y-chromosome (MCL-Y) is about 81 bp in length. As used herein, the term "about" refers to a range comprising +/−20% of the value of reference. Thus, said multicopy locus can have a length ranging from 65 to 95 bp.

Preferably, the method comprises the step of amplification of a multicopy locus within the Y-chromosome (MCL-Y), wherein said locus shares at least 85%, 90%, 95% or 99% sequence identity to a sequence according to SEQ ID NO. 3 over a stretch of at least 60 base pairs (bp) or with the reverse complement thereof.

The present method shows an improved sensibility over other commercially available methods. In particular, according to another embodiment the nucleic acid of a genome in a sample is detected and/or quantified at the lowest concentration of 0.125 pg/µl.

According to another embodiment of the present application, the amplification product of at least one nucleic acid is between 60 and 200 bp in length.

Preferably, the amplification step is performed using at least one primer selected from one of the groups consisting of (i) SEQ ID NO. 1 and SEQ ID NO. 2, (ii) a reverse complement of SEQ ID NO. 1 and SEQ ID NO. 2 and (iii) a primer that shares at least 90% sequence identity with one of the primers with SEQ ID NO. 1 and SEQ ID NO. 2 or a reverse complement thereof. These may be combined with a second overlapping amplicon wherein the primer pairs used have a sequence according to (iv) SEQ ID NO. 2 and SEQ ID NO. 13, SEQ ID NO. 2 and SEQ ID NO. 14, (v) and SEQ ID NO. 2 and SEQ ID NO. 15; see also FIG. 2. When measuring additionally degradation, the amplicon SEQ ID NO. 1 and 2 is combined with an amplicon selected from (i) SEQ ID NO. 2 and SEQ ID NO. 13, (ii) SEQ ID NO. 2 and SEQ ID NO. 14, or (iii) SEQ ID NO. 2 and SEQ ID NO. 15.

In a preferred embodiment the amplification reaction comprises amplifying at least two overlapping regions using at least one common primer, or two common primers or three common primer or more.

Preferably, the amplification step is performed using a primer pair selected from one of the groups consisting of (i) SEQ ID NO. 1 and SEQ ID NO. 2, (ii) a reverse complement of SEQ ID NO. 1 and SEQ ID NO. 2, and (iii) a primer that shares at least 90% sequence identity with one of the primers with SEQ ID NO. 1 and SEQ ID NO. 2 or a reverse complement thereof optionally combined with one or more of the pairs selected from (i) SEQ ID NO. 2 and SEQ ID NO. 13, (ii) SEQ ID NO. 2 and SEQ ID NO. 14, or (iii) SEQ ID NO. 2 and SEQ ID NO. 15.

Ideally, the amplification is performed using a primer pair with a sequence according to SEQ ID NO. 1 and SEQ ID NO. 2.

Preferably, the sample originates from one of the following tissues types comprising whole blood, blood fractions, oral specimen, urine, human bioptic tissue or other parts of the human body upon availability for isolation of a genome.

The best use of the sample is, e.g. a rape case wherein, said sample comprises male and female genomic DNA. The ratios of the amounts may be (male/female): 1/2, 1/3, 1/4, 1/10, 1/20, 1/50, 1/100, 1/1000, 1/5000, 1/10.000 or even 1/40.000, or even 1/400.000. It may also be (female/male): 1/2, 1/3, 1/4, 1/10, 1/20, 1/50, 1/100, 1/1000, 1/5000, 1/10.000 or even 1/40.000, or even 1/400.000. The method has shown to be able to identify 1 pg of male DNA in 400 ng of female DNA.

The present method also enables the detection and analysis of the degradation status of male DNA in non-degraded or also degraded female DNA.

Preferably, the amplification method is a polymerase chain reaction (PCR) or a real-time PCR reaction and the amount of nucleic acid determined is quantified either during the amplification process or as an end point measurement at the end of the amplification reaction.

At best the amplification reaction for carrying out the method of the present invention comprises:
a. Tris-HCl at a pH of between 8 and 8.8 and/or,
b. potassium salt selected from the group of, potassium chloride and potassium sulphate and/or,
c. an ammonium salt, preferably ammonium chloride or ammonium sulphate and/or,
d. magnesium chloride and/or,
e. a hot-start polymerase.

The invention relates to an oligonucleotide primer or primer pair, wherein at least one primer of said primer pair hybridizes under stringent conditions to a nucleic acid with a sequence according to SEQ ID NO. 3 to SEQ ID NO. 11 and/or 17 to 25. Preferably, both primers hybridize under stringent conditions.

As used herein, the term "stringent conditions" refer to conditions under which a nucleic acid having complementarity to a target sequence predominantly hybridizes with the target sequence and substantially does not hybridize to non-target sequences. Stringent conditions are generally sequence-dependent, and vary depending on a number of parameters, such as temperature, ionic strength and the presence of other compounds such as organic solvents, under which nucleic acid hybridizations are conducted. The person skilled in the art is familiar with such conditions, and thus they are not given here. Non-limiting examples of stringent conditions are described in detail in Tijssen (1993), Laboratory techniques in biochemistry and molecular biology—Hybridization with nucleic acid probes Part 1, second chapter "Overview of principles of hybridization and the strategy of nucleic acid probe assay", Elsevier, N.Y.

The invention also encompasses an oligonucleotide primer or primer pair for use in a method for detecting and/or quantifying DNA, in particular the fraction of male DNA, in a sample according to the first aspect of the present invention, wherein at least one primer, preferably both primers, of said primer pair hybridizes under stringent conditions to a nucleic acid with a sequence according to SEQ ID NO. 3 to SEQ ID NO. 11 and/or 17 to 25.

Claimed are the oligonucleotides with the following sequences SEQ ID NO. 1, 2, 12, 13, 14, 15 and 16 or oligonucleotides that share a sequence identity of no less than, 90%, 95% or 99% to these, or the reverse complement thereof.

According to another embodiment, claimed are oligonucleotides with the following sequences SEQ ID NO. 1, 2, 12, 13, 14, 15 and 16 or oligonucleotides that share a sequence identity of no less than, 90%, 95% or 99% to these, or the reverse complement thereof for use in a method for detecting and/or quantifying DNA, in particular the fraction of male DNA, in a sample according to the first aspect of the present invention.

Claimed is also a kit for performing a method according to any of the claims 1 to 10, wherein said kit comprises at least one oligonucleotide primer selected from the group consisting of SEQ ID NO. 1 and SEQ ID NO. 2, or a primer according to claim 9.

According to another embodiment, the sample subjected to the present method originates from one of the following specimens comprising whole blood, blood fractions, oral fluids, body fluids, human bioptic tissue or other parts of the human body upon availability for isolation of a genome. As used herein the terms "oral fluids" and "body fluids" refers to fluids that are excreted or secreted from the buccal cavity and from the body, respectively, from which a genome can be isolated. As a non-limiting example, oral and body fluids may comprise saliva, sputum, swab, urine.

In a preferred embodiment, the DNA or RNA analyzed is fragmented. In another embodiment, the DNA or RNA analyzed is in a composition with inhibitors.

As reported above, a typical forensic sample comprise a mixture of male and female DNA wherein the amount of female DNA exceeds the amount of male DNA by several orders of magnitude. Thus, according to another embodiment, the sample comprises one or more additional nucleic acids originating from a different genome. As used herein, the term "different genome" refers to genome isolated from a different subject, generally identified as female DNA.

According to another embodiment of the present invention, the amplification method is a polymerase chain reaction (PCR) or a real-time PCR reaction and the amount of nucleic acid determined is quantified either during the amplification process or as an end point measurement at the end of the amplification reaction.

The amplification reaction according to the present method may be either a non-isothermal method or an isothermal method.

The non-isothermal amplification method may be selected from the group of polymerase chain reaction (PCR) (Saiki et al. Science (1985) 230: 1350-1354), quantitative real-time PCR (rtPCR), ligase chain reaction (LCR) (Landegren et al. Science (1988) 241: 1077-1080). Polymerase chain reaction amplification is preferred.

The isothermal amplification method may be selected from the group of helicase-dependent amplification (HDA) (Vincent et al. EMBO Rep (2004) 5 (8): 795-800), thermostable HDA (tHDA) (An et al. J. Biol. Chem. (2005) 280 (32): 28952-28958), strand displacement amplification (SDA) (Walker et al. Nucleic Acids Res. (1992) 20 (7): 1691-1696), multiple displacement amplification (MDA) (Dean et al. Proc. Natl. Acad. Sci. USA (2002) 99 (8): 5261-5266), rolling-circle amplification (RCA) (Liu et al. J. Am. Chem. Soc. (1996) 118: 1587-1594), restriction aided RCA (Wang et al. Genome Res (2004) 14: 2357-2366), single primer isothermal amplification (SPIA) (Dafforn et al. Biotechniques (2004), 37 (5): 854-857), transcription mediated amplification (TMA) (Vuorinen et al. J. Clin. Microbiol. (1995) 33: 1856-1859), nicking enzyme amplification reaction (NEAR) (Maples et al. US2009017453), exponential amplification reaction (EXPAR) (Van Ness et al. Proc. Natl. Acad. Sci. USA (2003) 100 (8): 4504-4509), loop mediated isothermal amplification (LAMP) (Notomi et al. Nucleic Acids Res. (2000) 28 (12): e63), recombinase polymerase amplification (RPA) (Piepenburg et al. PloS Biol. (2006) 4 (7): 1115-1120), nucleic acid sequence based amplification (NASBA) (Kievits et al. J. Virol. Methods (1991) 35: 273-286), smart-amplification process (SMAP) (Mitani et al. Nat. Methods (2007) 4 (3): 257-262).

By "isothermal amplification reaction" in context of the present invention it is meant that the temperature does not significantly change during the reaction. In a preferred embodiment, the temperature of the isothermal amplification reaction does not deviate by more than 10° C., preferably by not more than 5° C., even more preferably not more than 2° C. during the main enzymatic reaction step where amplification takes place.

Depending on the method of isothermal amplification of nucleic acids different enzymes are required for the amplification reaction. Known isothermal methods for amplification of nucleic acids are the above mentioned, wherein the at least one mesophilic enzyme for amplifying nucleic acids under isothermal conditions is selected from the group consisting of helicase, mesophilic polymerases, mesophilic polymerases having strand displacement activity, nicking enzymes, recombination proteins, ligases, glycosylases and/or nucleases.

The amplification methods will comprise buffers, dNTPs or NTPs in addition to the enzymes required.

As used herein, the term "dNTP" refers to deoxyribonucleoside triphosphates. Non-limiting examples of such dNTPs are dATP, dGTP, dCTP, dTTP, dUTP, which may also be present in the form of labelled derivatives, for instance comprising a fluorescent label, a radioactive label, a biotin label. dNTPs with modified nucleotide bases are also encompassed, wherein the nucleotide bases are for example hypoxanthine, xanthine, 7-methylguanine, inosine, xanthinosine, 7-methylguanosine, 5,6-dihydrouracil, 5-methylcytosine, pseudouridine, dihydrouridine, 5-methylcytidine. Furthermore, ddNTPs of the above-described molecules are encompassed in the present invention.

As used herein, the term "NTP" refers to ribonucleoside triphosphates. Non-limiting examples of such NTPs are ATP, GTP, CTP, TTP, UTP, which may also be present in the form of labelled derivatives, for instance comprising a fluorescent label, a radioactive label, a biotin label.

According to another embodiment of the present invention, the amplification reaction comprises, (a) Tris-HCl at a pH of between 8 and 8.8 (at 20° C.) and/or, (b) potassium salt selected from the group of, potassium chloride and potassium sulphate and/or, (c) an ammonium salt, preferably ammonium chloride or ammonium sulphate and/or, (d) magnesium chloride and/or, (e) a hot-start polymerase.

Preferably, the concentration of Tris-HCl is in the range from 10 to 100 mM, most preferably in the range from 20 to 70 mM, the concentration of $K^+$ is in the range from 1-25 mM, most preferred in the range from 2.5 to 20 mM, the concentration of $NH_4^+$ in range from 1 to 40 mM, most preferred in the range from 2.5 to 30 mM, and a concentration of $Mg^{2+}$ of 0.5 mM to 8 mM in excess to the concentration of the four dNTP's, most preferred a concentration of $Mg^{2+}$ of 0.7 mM to 5 mM in excess to the concentration of the four dNTP's, a hot-start polymerase, preferentially a hot-start polymerase allowing a hot-start time of less than 5 min, most preferred below 2 min.

A second aspect of the present invention relates to a primer or primer pair for amplifying at least one nucleic acids comprising a multicopy locus within the human Y-chromosome (MLC-Y) selected from the group consisting of: 5' GAAAGGCCTCATCAGGGCTCAG 3' (SEQ ID NO 1) and 5' TCCTCACTGGGAAACATGAGGAATGAC 3' (SEQ ID NO 2).

According to an embodiment of the second aspect, at least one primer hybridizes under stringent conditions to a region of the Y-chromosome represented by multicopy loci according to SEQ ID NO. 3 to SEQ ID NO. 11.

According to a third aspect of the present invention, a kit for detecting and/or quantifying human nucleic acids is disclosed, wherein said kit comprises at least a primer, that under stringent conditions, binds a sequence that shares at least 80% sequence identity to a sequence according to SEQ ID NO. 3 to 11 over a stretch of 80 bp, wherein in an amplification reaction, at least one nucleic acid is amplified, the locus that is amplified is a multicopy locus within the human Y-chromosome (MCL-Y). Is important that the primer can bind at least SEQ ID NO. 3, 4, 5, 6, 7, 8, 9, 10 and/or SEQ ID NO. 11 or all of the above.

The invention further relates to a method for obtaining a degradation index for male DNA of at least 6 when measuring degraded DNA of 350 bp length and of at least 180 when measuring degraded male DNA of 150 bp length and concentration of 2.3 ng/μl.

Preferably in the method according to the invention, the assessment of the status of male DNA degradation and/or integrity of one or more nucleic acids in a sample is done in parallel with the the detection of the one or more nucleic acids that are quantified. Preferably, the method addresses the status of male DNA degradation and/or integrity even in the presence of high background female DNA. In a further embodiment, the method may also be used for non-invasive early determination of fetal sex.

The invention relates also in particular to assessing the status of male DNA in the sample. This is done to assess the integrity or degradation status of the male DNA in the sample. Thus, the invention relates also to the use of the primers and/or probes of FIG. 2 for this status analysis.

EXAMPLES

The commercially available quantification kits were set up and analyzed as described in the respective handbooks. A serial dilution of human DNAs (isolated from human blood from anonymous donors using the QIAamp Investigator Kit) and mixtures thereof at known concentrations was used as a template for all of the three kits.

FIG. 1 shows the superiority of the present method (Investigator Quantiplex Pro) compared to other methods available on the market due to its increased sensitivity.

The Investigator Quantiplex Pro method provides high accuracy to quantify all amounts of used template at their correct concentrations, especially at the lowest concentrations of 0.125 pg/µl were much more adequately quantified compared to the Quantifiler TRIO method (based on Quantifiler TRIO Kit from Applied Biosystems), which uses a multicopy target, and the PowerQuant method (based on PowerQuant Kit from Promega) which also uses a multicopy target. Quantifiler TRIO method (based on Quantifiler TRIO Kit from Applied Biosystems showed high fluctuations below 5 pg/µl and failed to quantify male DNA concentrations below 0.5 pg/µl in the presence of female DNA background. The PowerQuant method failed to quantify the male DNA fraction below 0.25 pg/µl in the presence or absence of background female DNA. 2 µl of given dilutions of the human reference DNA were used in each reaction. DNA amounts are given in concentrations (pg/µL) or as total amount per reaction.

FIGURES

Figure 1:
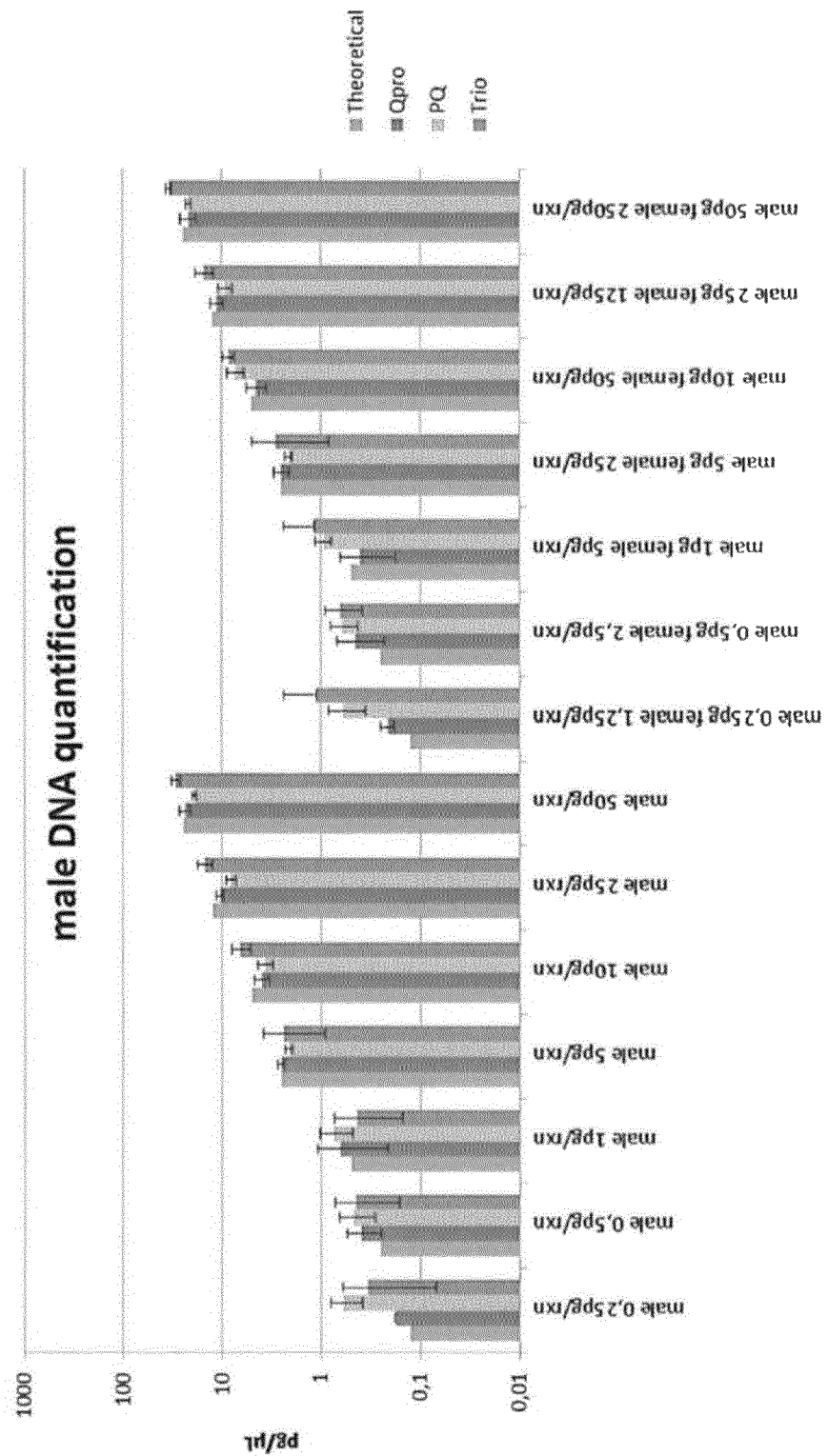
FIG. 1 shows the superiority of the present method (Investigator Quantiplex Pro) compared to other methods available on the market due to its increased sensitivity.
Figure 2:
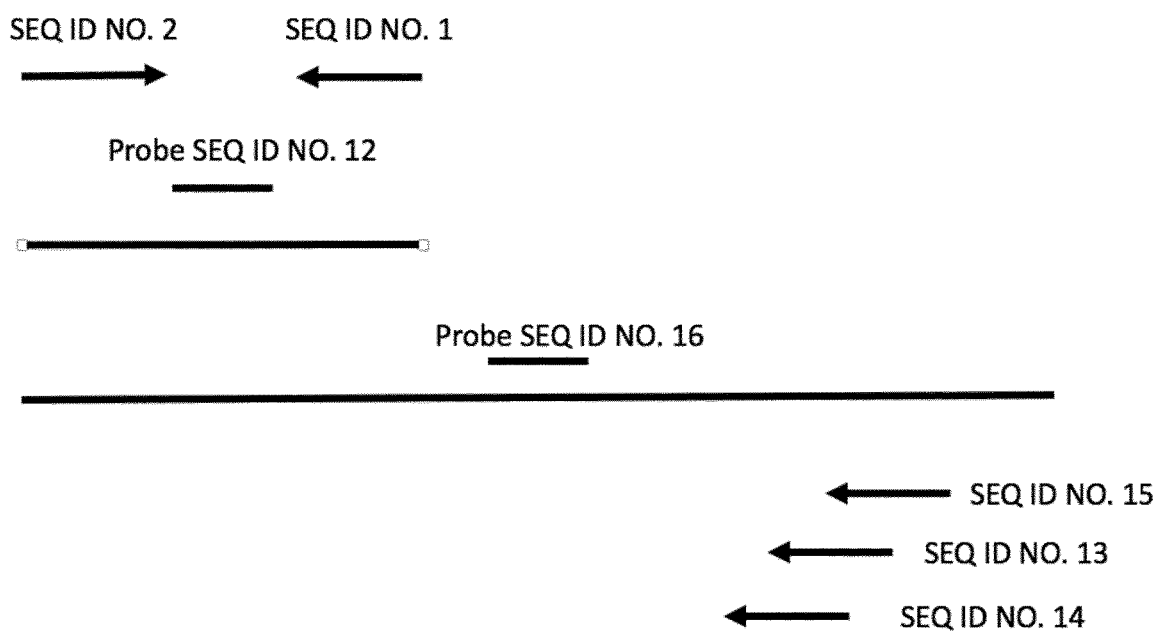
FIG. 2 shows a possible amplification set-up. It shows different combinations of primer pairs for the amplification of a multicopy locus within the Y-chromosome (MCL-Y).
Figure 3:
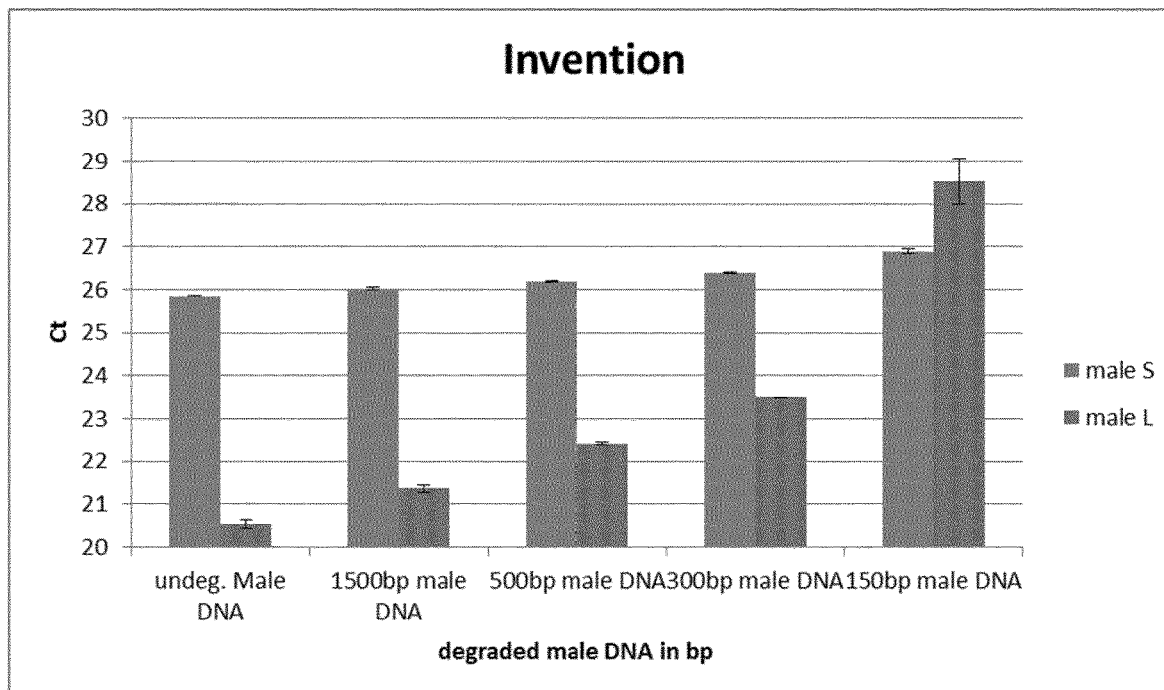

FIG. 3 Measurement of degraded male DNA according to the invention in humans

The invention shows no significant increase for the Ct values for the smallest PCR system (81 bp) for compromised DNA with an average fragment length from 1500 bp and 500 bp. Only for 300 bp and 150 bp there is an increase of Ct values. Surprisingly the larger PCR system (359 bp) shows already a significant shift of Ct values when applied on fragmented DNA of 1500 bp length. Furthermore, the Ct values increase consistently on every further tested fragment length from 500 bp, 300 bp, to 150 bp and reach their maximum at 150 bp with more than 8 Ct values compared to undegraded DNA. This allows for a precise assessment of the degradation or integrity status of male DNA. 2.3 ng/µl of male DNA was used for every fragment size or undegraded male DNA.

Figures 4, 5:
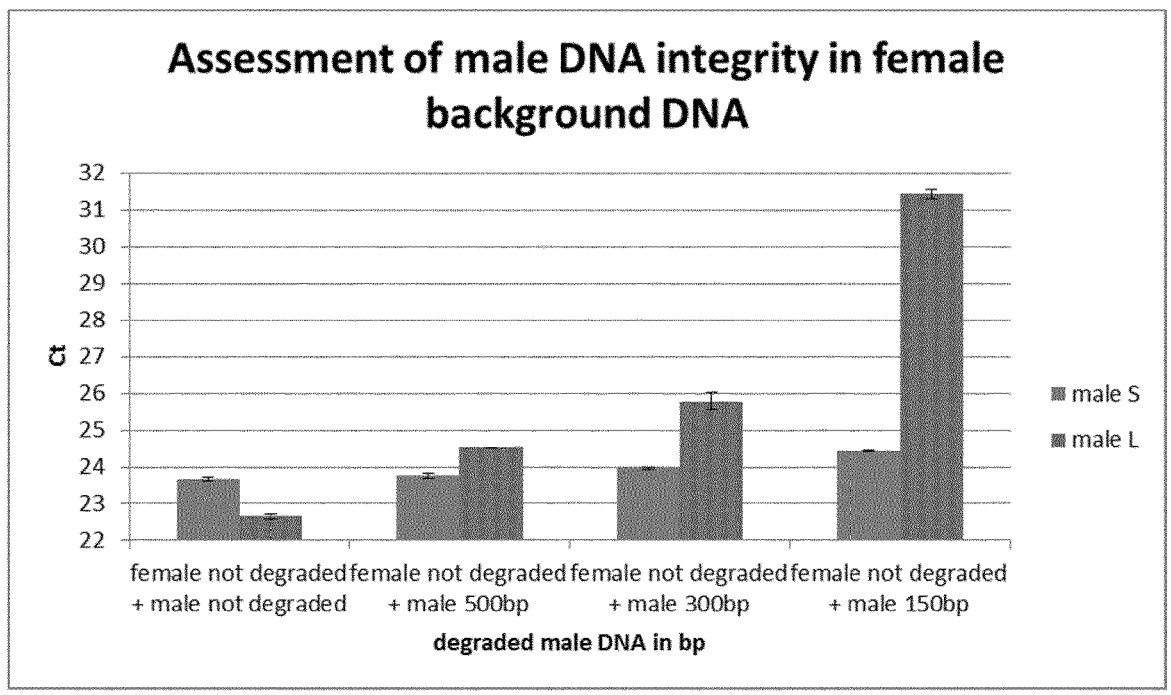

FIG. 4 Degradation index generated by the invention

Shown are the degradation indices (i.e. the ratio of the amount of short fragments vs. the amount of long fragments (male S/male L)) of the invention. Noticeably, the method according to the invention (second column) obtains extremely high indices, in particular for the small fragments (a value of almost 190, when 2.3 ng/µl of male DNA was tested). This indicates a high sensitivity for the detection of degraded male DNA.

FIG. 5 Measurement of degraded male DNA in background of female DNA in humans

Different fragmented male DNAs (each 0.76 ng/µl) have been spiked into non degraded female DNA (32 ng/µl). The invention shows no significant increase for the Ct values for the smallest PCR system (81 bp) for compromised DNA with an average fragment length for 500 bp. Only for 300 bp and 150 bp there is an increase of Ct values. Surprisingly the larger PCR system (359 bp) shows a significant shift of Ct values when applied on fragmented DNA of 500 bp length. Furthermore, the Ct values increase consistently on every further tested fragment length from 300 bp, to 150 bp and reach their maximum at 150 bp with more than 8 Ct values compared to undegraded DNA. This allows for a precise assessment of the degradation or integrity status of male DNA in female background DNA.

Figure 6:
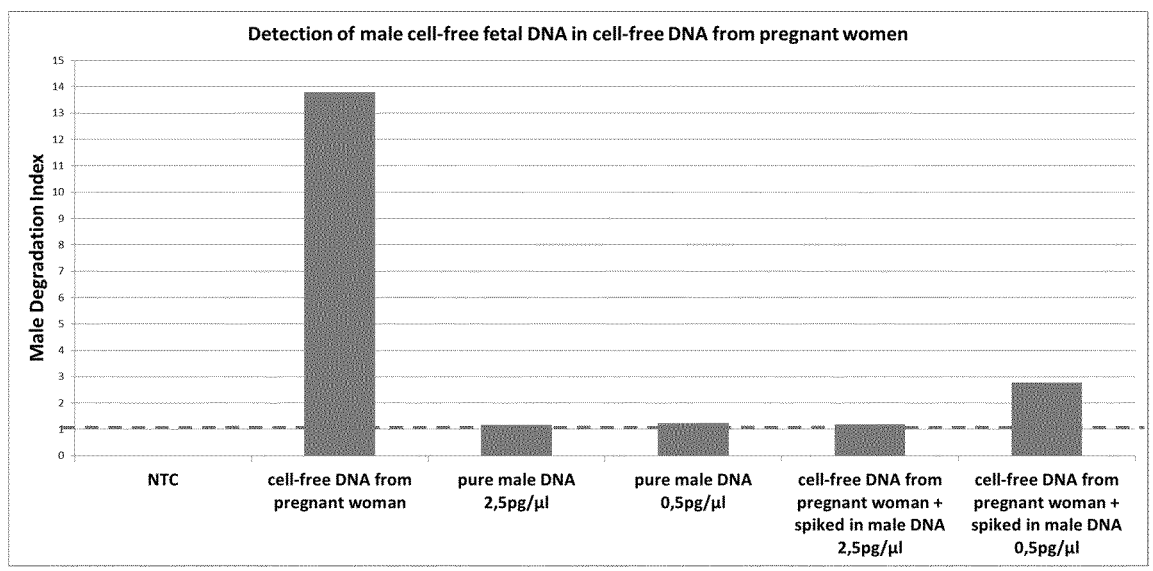

FIG. 6 Detection of male cell-free fetal DNA in cell-free DNA from pregnant women Shown is the Degradation Index (DI) generated by applying the invention on isolated cell free DNA from a pregnant woman. The system is able to detect low amounts of male DNA with both PCR systems for male targets, the small (81 bp) and the large one (359 bp). The small system detects the male cell free fetal DNA which is sized between 150-220 bp. The large male PCR system performs similarly to the small PCR system only on pure male genomic DNA or on contaminating male genomic DNA (spike in controls); on male cell free fetal DNA the performance will significantly drop due to the size limitation of the fragments of male cell-free fetal DNA in the cell-free DNA from pregnant women. This generates a high Degradation Index (DI) for non-contaminated cell-free DNA from women pregnant with a male embryo and a lower degradation index for contaminated cell-free DNA from women pregnant with a male or female embryo.

The invention claimed is:

1. A method for detecting, assessing the status of and/or quantifying the fraction of male DNA in a sample, wherein the method comprises amplification of a multicopy locus within the Y-chromosome (MCL-Y), and wherein the amplification is performed using at least one primer selected from the group consisting of:
   a. SEQ ID NO. 1;
   b. SEQ ID NO. 2;
   c. the reverse complement of SEQ ID NO. 1;
   d. the reverse complement of SEQ ID NO. 2;
   e. a primer that shares at least 90% sequence identity with SEQ ID NO. 1;
   f. a primer that shares at least 90% sequence identity with SEQ ID NO. 2;
   g. the reverse complement of a primer that shares at least 90% sequence identity with SEQ ID NO. 1; and
   h. the reverse complement of a primer that shares at least 90% sequence identity with SEQ ID NO. 2.

2. The method according to claim 1, wherein the amplification is performed using a primer pair selected from one of the groups consisting of:
   a. SEQ ID NO. 1 and SEQ ID NO. 2;
   b. the reverse complement of SEQ ID NO. 1 and the reverse complement of SEQ ID NO. 2;
   c. a primer that shares at least 90% sequence identity with SEQ ID NO. 1 and a primer that shares at least 90% sequence identity with SEQ ID NO. 2; and
   d. the reverse complement of a primer that shares at least 90% sequence identity with SEQ ID NO. 1 and the reverse complement of a primer that shares at least 90% sequence identity with SEQ ID NO. 2.

3. The method according to claim 1, wherein the amplification step is performed using a primer pair having a sequence according to SEQ ID NO. 1 and SEQ ID NO. 2.

4. The method according to claim 1, wherein said sample originates from whole blood, a blood fraction, an oral specimen, urine, human bioptic tissue or another part of a human body from which a genome is isolatable.

5. The method according to claim 1, wherein said sample comprises male and female genomic DNA.

6. The method according to claim 1, wherein the amplification step is performed by a polymerase chain reaction (PCR) or a real-time PCR reaction and the amount of nucleic acid determined is quantified either during the amplification process or as an end point measurement at the end of the amplification reaction.

7. The method according to claim 6, wherein the amplification reaction comprises any one or more of:
   a. Tris-HCl at a pH of between 8 and 8.8;
   b. a potassium salt selected from the group of potassium chloride and potassium sulfate;
   c. an ammonium salt;
   d. magnesium chloride; and
   e. a hot-start polymerase.

8. The method according to claim 6, wherein the amplification reaction comprises amplifying at least two overlapping regions using at least one common primer.

* * * * *